US006884214B2

(12) United States Patent
Itagaki

(10) Patent No.: US 6,884,214 B2
(45) Date of Patent: Apr. 26, 2005

(54) DAILY-LIFE DISABILITY RELATED PHYSICAL INFORMATION DETERMINING APPARATUS

(75) Inventor: Shuji Itagaki, Saitama (JP)

(73) Assignee: Tanita Corporation, Tokyo (JP)

( * ) Notice: Subject to any disclaimer, the term of this patent is extended or adjusted under 35 U.S.C. 154(b) by 199 days.

(21) Appl. No.: 10/274,272

(22) Filed: Oct. 21, 2002

(65) Prior Publication Data

US 2003/0088197 A1 May 8, 2003

(30) Foreign Application Priority Data

Oct. 23, 2001 (JP) ........................................ 2001-324519
Mar. 11, 2002 (JP) ........................................ 2002-065109

(51) Int. Cl.[7] ................................................ A61B 5/00
(52) U.S. Cl. ........................ 600/300; 600/547; 178/920
(58) Field of Search ................................ 600/300–301, 600/547, 585, 595; 482/8–9; 177/25, 245; 128/920–921; 73/379.01

(56) References Cited

U.S. PATENT DOCUMENTS

| 4,882,677 A | * 11/1989 | Curran ..................... 73/379.01 |
| 6,490,481 B1 | 12/2002 | Komatsu et al. |
| 6,532,384 B1 | 3/2003 | Fukuda |

FOREIGN PATENT DOCUMENTS

| EP | 1027860 A1 | 8/2000 |
| EP | 1080686 A1 | 3/2001 |
| JP | 2001-70273 | 3/2001 |
| JP | 2001-070273 | 3/2001 |
| JP | 2001-178696 | 7/2001 |
| JP | 2001-321343 | 11/2001 |

OTHER PUBLICATIONS

Corbeil C. et al., "Increased Risk for Falling Associated with Obesity: Mathematical Modeling of Postural Control," IEEE Transactions on Neural Systems and Rehabilitation Engineering, vol. 9, No. 2, Jun. 2001, pp. 126–136.
Fiatarone Maria A., et al. "The Boston FICSIT Study: The Effects of Resistance training and Nutritional Supplementation on Physical Frailty in the Oldest Old." JAGS–Mar. 1993–vol. 41, No. 3, pp. 333–337.
Winters Kerri M., et al. "Body Composition Predicts Bone Mineral Density and Balance in Premenopausal Women." Journal of Women's Health and Gender Based–Medicine, vol. 9, No. 8, 2000, Mary Ann Liebert Inc., pp 865–872/.
Bross, Rachelle., et al. "Aging and Muscle Loss." TEM vol. 10, No. 5, 1995, pp. 194–198.
European Search Report dated Feb. 20, 2003.

(Continued)

Primary Examiner—Eric F. Winakur
Assistant Examiner—Michael Astorino
(74) Attorney, Agent, or Firm—McDermott Will & Emery LLP

(57) ABSTRACT

An apparatus firstly acquires a value involving in a physical condition, such as a value relating to a body constitution, a value relating to a basic physical strength or a value relating to a motive ability, by acquisition means 101, secondly, based on said value, the apparatus specifies in specification means 103 the physical information involving in the physical strength related phase of the daily-life disability, such as a value relating to the basic strength, a value relating to the motive ability, or a value relating to a daily-life disability, all of which are configured for an aged person placed as a subject and stored in storage means 102, and finally the apparatus in output means 104 outputs thus specified information. Thereby, the determination on the physical information relating to the physical strength related phase of the daily-life disability may become possible automatically.

14 Claims, 17 Drawing Sheets

OTHER PUBLICATIONS

"Design Considerations for an Alert System to Prevent Inpatients Falls", H.F. Marin et al., AMIA 1997 Annual Fall Symposium, Oct. 25–29, Nashville, USA, 'Online! 1997, http//www.amia.org/pubs/symposia/D004100.pdf.

"Falling Risk Evaluation in Elderly Using Miniature Gyroscope", B. Najafi et al., 1st Annual International IEEE–EMBS Special Topic Conference on Microtechnologies in Medicine and Biology, Oct. 12–14, 2000, pp. 557–561.

"Continuous assessment of the risk of falling using telecare", Kevin Doughty et al., Journal of Telemedicine and Telecare, England 1998, voi. 4 Suppl 1, pp. 88–90.

"Risk of fracture in elderly patients: a new predictive index based on bone mineral density and finite element analysis", D. Testi et al., Computer Methods and Programs in Biomedicine, Jul. 1999, vol. 60, No. 1, pp. 23–33.

"Body Size and Hip Fracture Risk in Older Women: A Prospective Study", The American Journal of Medicine. Oct. 1997, vol. 103, No. 4, pp. 274–280.

"Quantitative Assessment of Forearm Muscle Size, Forelimb Grip Strength, Forearm Bone Mineral Density, and Forearm Bone Size in Determining Humerous Breaking Strength in 10 Inbred Strains of Mice", X. Li et al., Calcified Tissue International, Jun. 2001, vol. 68, No. 6, pp. 365–369.

"Assessment of patients who fall", Kane et al., Essentials of Clinical Geriatrics, 2nd Edition, Online! 1989, http://www.universityhospital.org/geriatric_education/library/falls.pdf.

* cited by examiner

FIG. 3

| RESULT OF ACTIVE MOTION DISABLED LEVEL | FIRST ADVICE INFORMATION |
|---|---|
| $1 \leq Y < 2$ | "GOOD. HOLD ON THE CURRENT STATE." |
| $2 < Y \leq 3$ | "YOU NEED SOME CARE. PAY ATTENTION TO YOUR STEPS AND WALK CAREFULLY." |
| $3 \leq Y$ | "YOU MUST NEED ADEQUATE CARE. PAY ATTENTION TO YOUR STEPS MORE CAREFULLY AND WALK WITH SOME ASSISTANCE IN RELAXING MOOD." |

FIG. 4

| RESULT OF VALUE RELEVANT TO PHYSICAL CONDITION | | SECOND ADVICE INFORMATION |
|---|---|---|
| PERCENT BODY FAT | $S1 \leq X_1$ | "TOO HIGH PERCENT FAT OF ENTIRE BODY. THINK OVER YOUR DIETARY HABIT." |
| | $S2 < X_1 < S1$ | "APPROPRIATE PERCENT FAT OF ENTIRE BODY. HOLD ON THE CURRENT STATE." |
| | $X_1 \leq S2$ | "TOO LOW PERCENT FAT OF ENTIRE BODY. TAKE WELL-BALANCED MEALS AND SAVE ENERGY." |
| LEG LEAN BODY MASS OR LEAN BODY MASS | $S3 \leq X_2$ | "QUITE SUFFICIENT MUSCLE MASS OF LEG. HOLD ON THE CURRENT STATE." |
| | $S4 < X_2 < S3$ | "STANDARD LEVEL OF MUSCLE MASS OF LEG. KEEP AN APPROPRIATE AMOUNT OF EXERCISE." |
| | $X_2 \leq S4$ | "DECREASING MUSCLE MASS OF LEG. TAKE A LEG TRAINING REGULARLY." |
| GRAVITY CENTER SWAY DISTANCE | $S5 \leq X_3$ | "VERY BAD BODY BALANCE. BE CAREFUL IN DAILY-LIFE WITH ATTENTION ON YOUR STEPS." |
| | $S6 < X_3 < S5$ | "STANDARD BODY BALANCE. KEEP GOING WITH THE REGULAR LIFE." |
| | $X_3 \leq S6$ | "VERY GOOD BODY BALANCE. HOLD ON THE CURRENT STATE." |

FIG. 7

| RESULT | |
|---|---|
| PERCENT BODY FAT | XX.X % |
| LEG LEAN BODY MASS (OR LEAN BODY MASS) | XX.X kg/m² |
| INTRACELLULAR FLUID VOLUME | XX.X kg |
| EXTRACELLULAR FLUID VOLUME | XX.X kg |
| GRAVITY CENTER SWAY DISTANCE | XXX cm |
| PULSE DIFFERENTIAL COUNT BET. SITTING POSITION AND STANDING POSITION | XXX pulse/min |
| ACTIVE MOTION DISABLED LEVEL | X.X |

| YOUR PERSONAL INFORMATION | |
|---|---|
| PERSONAL NO. | XX |
| SEX | X |
| AGE | X |
| HEIGHT | XX cm |

| RESULT OF ACTIVE MOTION DISABLED LEVEL | COLOR USED IN GRAPHICAL REPRESENTATION OF THE ACTIVE MOTION DISABLED LEVEL |
|---|---|
| $1 \leq Y < 2$ | BLUE |
| $2 < Y \leq 3$ | YELLOW |
| $3 \leq Y$ | RED |

FIG. 10

| ACTIVE MOTION DISABLED LEVEL | VALUE RELATING TO PHYSICAL CONDITION | | |
|---|---|---|---|
| | PERCENT BODY FAT | LEG LEAN BODY MASS OR LEAN BODY MASS | GRAVITY CENTER SWAY DISTANCE |
| Y1 | $X_1 \leq 27$ | $7.26 < X_2$ | $X_3 \leq 30$ |
| Y2 | $X_1 \leq 27$ | $7.26 < X_2$ | $30 < X_3$ |
| Y3 | $X_1 \leq 27$ | $X_2 \leq 7.26$ | $X_3 \leq 30$ |
| Y4 | $X_1 \leq 27$ | $X_2 \leq 7.26$ | $30 < X_3$ |
| Y5 | $27 < X_1$ | $7.26 < X_2$ | $X_3 \leq 30$ |
| Y6 | $27 < X_1$ | $7.26 < X_2$ | $30 < X_3$ |
| Y7 | $27 < X_1$ | $X_2 \leq 7.26$ | $X_3 \leq 30$ |
| Y8 | $27 < X_1$ | $X_2 \leq 7.26$ | $30 < X_3$ |

US 6,884,214 B2

DAILY-LIFE DISABILITY RELATED PHYSICAL INFORMATION DETERMINING APPARATUS

BACKGROUND OF THE INVENTION

1. Field of the Invention

The present invention relates to a daily-life disability related physical information determining apparatus, which based on a physical condition, makes a determination on the physical information relating to a physical strength related phase of a daily-life disability. The present invention further relates to such a daily-life disability related physical information determining apparatus which based on a plurality of different types of physical conditions, makes a determination on an occurrence rate of potential disability in a daily activity, as an exemplary example of said apparatus, which based on a physical condition, makes a determination on the physical information relating to the physical strength related phase of the daily-life disability.

2. Description of the Related Art

Researches in recent years have unveiled a fact that, especially in the aged person, a physical strength or an athletic ability deteriorates with aging, and this condition in turn could make the aged person suffer from such a disability that he/she may fall down and eventually have his/her bone broken. In this regard, in order to know the occurrence rate of such a potential disability with respect to an active motion in the daily life, such a method has been employed as a common practice, in which, primarily, a physical strength and/or an athletic ability is measured under instructions of a specialist such as a physician, and then data is referred, which indicates a relationship between the physical strength and/or the athletic ability and the occurrence rate of the disability with respect to the active motion, thereby recognizing the occurrence rate of the disability with respect to the active motion corresponding to the measured physical strength and/or athletic ability.

However, the above-described method for grasping the occurrence rate of the disability with respect to the active motion has required to measure the physical strength and/or the athletic ability with a relatively large load applied to the body of a subject. Further disadvantageously, the above method has to be executed under the instructions of the specialist as a physician and such a data should be referred, which indicates a relationship between the physical strength and/or the athletic ability and the occurrence rate of the disability with respect to the active motion. Those works are rather troublesome to be practiced actually, which means that this method is not a simple method.

SUMMARY OF THE INVENTION

It is an object of the present invention to provide a daily-life disability related physical information determining apparatus, which allows to make in a simple manner a determination on physical information relating to a physical strength related phase of a daily-life disability.

It is another object of the present invention to provide a daily-life disability related physical information determining apparatus, which allows to make in a simple manner a determination on an occurrence rate of a disability with respect to an active motion as an exemplary example of the determination on the physical information relating to the physical strength related phase of a daily-life disability.

It is a further object to provide a daily-life disability related physical information determining apparatus, comprising acquisition means, storage means, specification means and output means, wherein said acquisition means acquires values relating to a plurality of different types of physical conditions; said storage means stores active motion disabled levels, which have been associated with the values relating to said plurality of different type of physical conditions acquired by said acquisition means; said specification means specifies the active motion disabled level stored in said storage means based on the values relating to said plurality of different types of physical conditions acquired by said acquisition means; and said output means outputs the active motion disabled level specified by said specification means. According to this configuration, since the active motion disabled level stored in the storage means can be specified based on the values relating to the plurality of different types of physical conditions acquired by the acquisition means, therefore a determination on the active motion disabled level may become possible automatically.

According to one embodiment of the present invention, said acquisition means is at least either one of input means or measuring means. According to this embodiment, the value relating to the physical condition can be obtained easily.

According to another embodiment of the present invention, said storage means further stores first advice information associated with said active motion disabled level, said specification means further specifies the first advice information stored in said storage means on the basis of the previously specified active motion disabled level, and said output means further outputs the first advice information specified by said specification means. According to this embodiment, since the first advice information stored in the storage means can be specified by the specification means based on the active motion disabled level acquired by the specification means, therefore an automatic reception of the first advice information on the active motion disabled level may become possible.

According to another embodiment of the present invention, said storage means further stores second advice information associated with a value relating to each individual physical condition among those values relating to said plurality of different types of physical conditions, said specification means further specifies the second advice information based on the value relating to each individual physical condition among said plurality of different types of conditions acquired by said acquisition means, and said output means further outputs the second advice information specified by said specification means. According to this embodiment, since the second advice information stored in the storage means can be specified by the specification means based on the value relating to each individual physical condition among the plurality of different types of physical conditions acquired by the acquisition means, therefore an automatic reception of the second advice information on each individual physical condition may become possible.

According to still another embodiment of the present invention, said active motion disabled levels are associated with said values relating to said plurality of different types of physical conditions, said values generated in such a way that a value relating to at least one type of physical condition weights a value relating to another type of physical condition. According to this embodiment, since a degree of contribution of the value relating to each individual physical condition to the active motion disabled level can be modified through the operation of weighting, therefore a higher accuracy in estimation may be obtained.

According to another embodiment of the present invention, said active motion disabled level is configured for an aged person placed as a subject. According to this embodiment, by limiting the active motion disability to that having a higher occurrence rate particular in the aged person as the subject, the apparatus may be of higher utility value.

According to another embodiment of the present invention, said output means is display means for indicating a result specified by said specification means. According to this embodiment, since the result is indicated by the display means, therefore the result can be visually perceived.

According to another embodiment of the present invention, said display means provides said active motion disabled level in a graphical representation. According to this embodiment, since the active motion disabled level is indicated in the form of a graph, therefor the result may be easily turned into an image thus facilitating the perception thereof.

According to another embodiment of the present invention, said display means provides said active motion disabled level in a graphical representation, which is associated with an axis of graph representing to a value relating to each individual physical condition among the values relating to the plurality of different types of physical conditions acquired by said acquisition means. According to this embodiment, a relation between the value relating to each individual physical condition among the values relating to a plurality of different types of physical conditions and the active motion disabled level can be grasped easily.

According to another embodiment of the present invention, said values relating to said plurality of different types of physical conditions are representative of at least two values selected from a group consisting of those values relating to a muscle, a body fat, a lean body, a leg lean body, a gravity center stability, an intracellular fluid, an extracellular fluid, and a pulse differential between sitting position and standing position, respectively. According to this embodiment, since the muscle, the body fat, the lean body, the leg lean body, the gravity center stability, the intracellular fluid, the extracellular fluid, and the pulse differential between sitting position and standing position have good relationship respectively with the active motion disabled level, therefore a highly accurate result can be obtained. In addition, the values relating to the muscle, the body fat, the leg lean body, the gravity center stability, the intracellular fluid, the extracellular fluid, and the pulse differential between sitting position and standing position can be measured respectively in a simple manner particularly with only a small load to the body.

It is a further object of the present invention to provide a daily-life disability related physical information determining apparatus comprising acquisition means, storage means, specification means and output means, wherein said acquisition means acquires a value relating to a physical condition; said storage means stores physical information on a physical strength related phase of a daily-life disability, said physical information associated with the value relating to said physical condition; said specification means specifies the physical information on the physical strength related phase of the daily-life disability stored in said storage means based on the value relating to the physical condition acquired by said acquisition means; and said output means outputs the physical information on the physical strength related phase of the daily-life disability specified by said specification means. According to this configuration, since the physical information on the physical strength related phase of the daily-life disability stored in the storage means is specified by the specification means based on the value relating to the physical condition acquired by the acquisition means, therefore a determination on the physical strength related phase of the daily-life disability may become possible automatically.

According to one embodiment of the present invention, said storage means further stores another physical information on the physical strength related phase of the daily-life disability, said physical information having been associated with the previous physical information on the physical strength related phase of the daily-life disability, and said specification means further specifies another physical information on the physical strength related phase of the daily-life disability, which has been stored in said storage means, based on the previously specified physical information on the physical strength related phase of the daily-life disability. According to this embodiment, since another physical information on the physical strength related phase of the daily-life disability stored in the storage means can be further specified by the specification means on the basis of the physical information on the physical strength related phase of the daily-life disability specified previously by the specification means, therefore a determination on the physical information about the physical strength related phase of the daily-life disability of many different types may become possible automatically.

According to another embodiment of the present invention, said acquisition means is at least either one of input means or measuring means. According to this embodiment, the value relating to the physical condition can be obtained easily by an input operation and/or a measuring operation.

According to still another embodiment of the present invention, said output means is display means for indicating a result specified by said specification means. According to this embodiment, since the result is indicated by the display means, therefore the result can be visually perceived.

According to another embodiment of the present invention, said display means provides said physical information on the physical strength related phase of the daily-life disability in a graphical representation. According to this embodiment, since the physical information on the physical strength related phase of the daily-life disability is indicated in the form of a graph, therefor the result may be easily turned into an image thus facilitating the perception thereof.

According to another embodiment of the present invention, said physical information on the physical strength related phase of the daily-life disability is configured for an aged person placed as a subject. According to this embodiment, by limiting the physical information on the physical strength related phase of the daily-life disability to that for the aged person placed as a subject, who particularly has a higher occurrence rate of the daily-life disability, the apparatus may be of higher utility value.

According to another embodiment of the present invention, said value relating to the physical condition is representative of at least one selected from a group consisting of those values relating to a body constitution, a basic physical strength, and a motive ability, respectively, and said physical information on the physical strength related phase of the daily-life disability is representative of at least one selected from a group consisting of those values relating to a basic physical strength, a motive ability and a daily-life disability, respectively. According to this embodiment, since especially, the value relating to the body constitution, the value relating to the basic physical strength and the value relating to the motive ability, which are given as the values relating to the physical condition, have good relationship with the value relating to the basic physical strength, the value relating to the motive ability and the value relating to the daily-life disability, which are given as the physical information on the physical strength related phase of the daily-life disability, therefore a highly accurate result can be obtained.

According to another embodiment of the present invention, said value relating to the body constitution is representative of at least one selected from a group consisting of a lean body mass, a muscle mass and a BCM, said value relating to the basic physical strength is representative of at least either one of a muscle strength or an equilibration, said value relating to the motive ability is representative of a walking ability, and said value relating to the daily-life disability is representative of at least one selected from a group consisting of a fall-down disabled level, a bone fracture disabled level, an osteoporosis disabled level, a hyperlipemia disabled level and an active motion disabled level. According to this embodiment, since the lean body mass, the muscle mass, the BCM, the muscle strength, the equilibration and the walking ability presented as the values relating specifically to the physical condition have especially good relationship with the muscle strength, the equilibration, the walking ability, the fall-down disabled level, the bone fracture disabled level, the osteoporosis disabled level, the hyperlipemia disabled level and the active motion disabled level presented as the physical information on the physical strength related phase of the daily-life disability, therefore, particularly a highly accurate result can be obtained.

It is a still further object of the present invention to provide a daily-life disability related physical information determining apparatus, comprising acquisition means, storage means, specification means and output means, wherein said acquisition means acquires a value relating to a physical condition as well as secondary physical information; storage means stores physical information on a physical strength related phase of a daily-life disability, said physical information associated with the value relating to said physical condition as well as said secondary physical information; said specification means specifies the physical information on the physical strength related phase of the daily-life disability stored in said storage means based on the value relating to the physical condition as well as the secondary physical information acquired by said acquisition means; and said output means outputs the physical information on the physical strength related phase of the daily-life disability specified by said specification means. According to this configuration, since the physical information on the physical strength related phase of the daily-life disability stored in the storage means can be specified by the specification means based on the value relating to the physical condition as well as the secondary physical information acquired by the acquisition means, therefore a determination on the physical information about the physical strength related phase of the daily-life disability may become possible automatically, and further, since the determination is made by taking not only the value relating to the physical condition but also the secondary physical information into account, a highly accurate result can be obtained.

According to one embodiment of the present invention, wherein said storage means further stores another physical information on the physical strength related phase of the daily-life disability, said physical information having been associated with the previous physical information on the physical strength related phase of the daily-life disability as well as said secondary physical information, and said specification means further specifies another physical information on the physical strength related phase of the daily-life disability stored in said storage means based on the previously specified physical information on the physical strength related phase of the daily-life disability as well as said secondary physical information acquired by said acquisition means. According to this embodiment, since another physical information on the physical strength related phase of the daily-life disability stored in said storage means can be further specified by the specification means based on the physical information on the physical strength related phase of the daily-life disability previously specified by the specification means as well as said secondary physical information acquired by said acquisition means, therefore a highly accurate determination on the physical information on the physical strength related phase of the daily-life disability of various types may become possible automatically, and further, since the determination is made by taking not only the value relating to the physical condition but also the additional secondary physical information into account, a highly accurate result can be obtained.

According to another embodiment of the present invention, said acquisition means is at least either one of input means or a measuring means. According to this mode, the value relating to the physical condition and/or the secondary physical information can be obtained easily by an input operation and/or a measuring operation.

According to still another embodiment of the present invention, said output means is display means for indicating a result specified by said specification means. According to this mode, since the result is indicated by the display means, therefore the result can be visually perceived.

According to still another embodiment of the present invention, wherein said display means provides said physical information on the physical strength related phase of the daily-life disability in a graphical representation. According to this embodiment, since the physical information on the physical strength related phase of the daily-life disability is indicated in the form of a graph, therefore the result can be easily turned into an image thus facilitating the perception thereof.

According to another embodiment of the present invention, said physical information on the physical strength related phase of the daily-life disability is configured for an aged person placed as a subject. According to this embodiment, by limiting the physical information on the physical strength related phase of the daily-life disability to that for the aged person placed as a subject, who particularly has a higher occurrence rate of the daily-life disability, the apparatus may be of higher utility value.

According to another embodiment of the present invention, said value relating to the physical condition is representative of at least one selected from a group consisting of those values relating to a body constitution, a basic physical strength, and a motive ability, respectively, and said physical information on the physical strength related phase of the daily-life disability is representative of at least one selected from a group consisting of those values relating to a basic physical strength, a motive ability and a daily-life disability, respectively. According to this embodiment, since especially the value relating to the body constitution, the value relating to the basic physical strength and the value relating to the motive ability presented as the values relating to the physical condition have good relationship with the value relating to the basic physical strength, the value relating to the motive ability and the value relating to the daily-life disability presented as the physical information on the physical strength related phase of the daily-life disability, therefore an extremely highly accurate result can be obtained.

According to another embodiment of the present invention, said value relating to the body constitution is representative of at least one selected from a group consisting of a lean body mass, a muscle mass and a BCM, said value relating to the basic physical strength is representative of either one of a muscle strength or an equilibration, said value relating to the motive ability is representative of a walking ability, said value relating to the daily-life disability is representative of at least one selected from a group consisting of a fall-down disabled level, a bone fracture disabled level, an osteoporosis disabled level, a hyperlipemia disabled level and an active motion disabled level, and said secondary physical information is representative of at least one selected from a group consisting of an age, a sex, a height and a body weight. According to this embodiment, since especially the lean body mass, the muscle mass, the BCM, the muscle strength, the equilibration and the walking ability, each presented as the values relating to the physical condition as well as the age, the sex, the height, and the body weight, each presented as the secondary physical information have particularly good relationship with the muscle strength, the equilibration, the walking ability, the fall-down disabled level, the bone fracture disabled level, the osteoporosis disabled level, the hyperlipemia disabled level and the active motion disabled level, each presented as the physical information on the physical strength related phase of the daily-life disability, therefore, particularly an extremely highly accurate result can be obtained.

BRIEF DESCRIPTION OF THE DRAWINGS

FIG. 3 shows an example of first advice information associated with active motion disabled levels;

FIG. 4 shows an example of second advice information associated with the values relating to each individual physical condition;

FIG. 7 shows an example of an indication on a screen for a currently determined result;

FIG. 10 is a corresponding relation table between the active motion disabled level and the values relating to a plurality of different types of physical conditions;

DETAILED DESCRIPTION OF THE PREFERRED EMBODIMENT

A daily-life disability related physical information determining apparatus according to the present invention is such an apparatus which makes a determination on physical information relating to a physical strength related phase of a daily-life disability on the basis of a value relating to the physical condition. Preferred embodiments of the present invention will now be described in detail with reference to the attached drawings.

First of all, as a first embodiment of the present invention, an active motion disability determining apparatus will be described in detail, which is one of the specific types of daily-life disability related physical information determining apparatuses and has an aspect in which an active motion disabled level is determined as the physical information on the physical strength related phase of the daily-life disability based on values relating to a plurality of different types of physical conditions.

Figure 1:
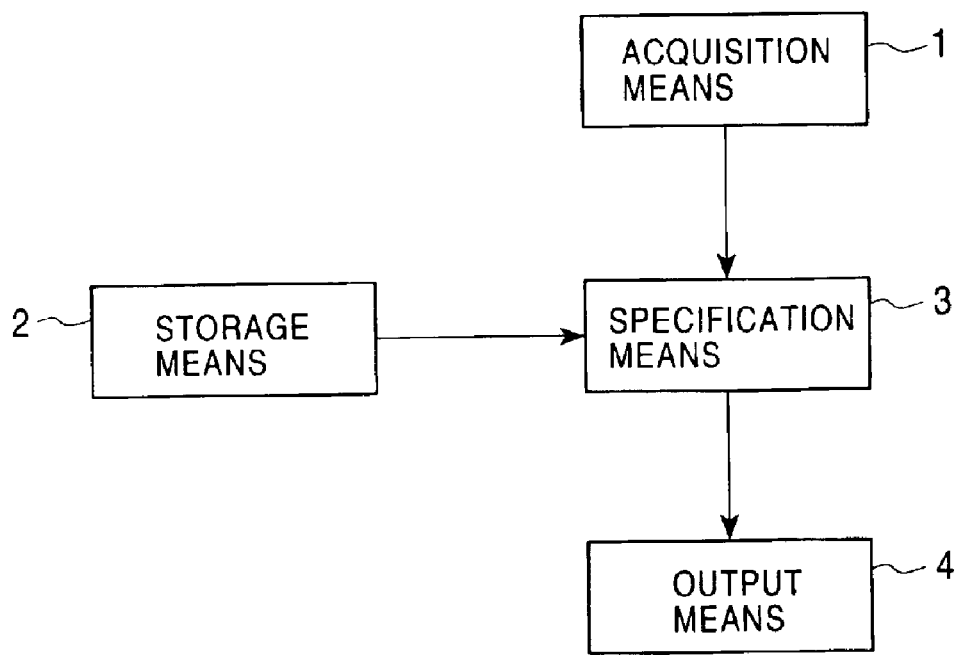
FIG. 1 is a block diagram illustrating a configuration of an active motion disability determining apparatus according to (a first embodiment of) the present invention.
Figure 2:
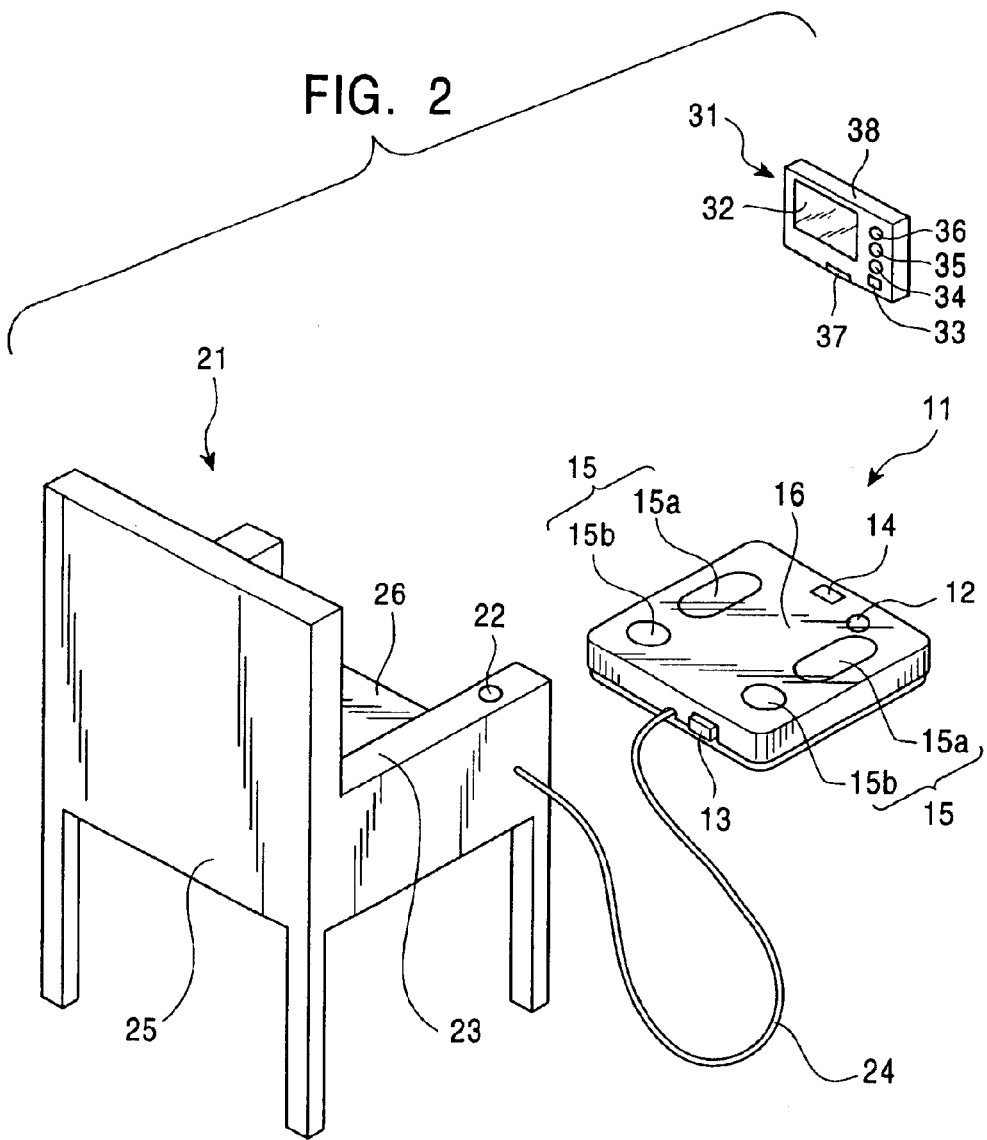
FIG. 2 is an overview of the active motion disability determining apparatus according to (the first embodiment of) the present invention.

To begin with, a configuration of the active motion disability determining apparatus according to the present invention is shown in FIG. 1 in a form of block diagram, and an overview thereof is shown in FIG. 2. The active motion disability determining apparatus according to the first embodiment of the present invention comprises acquisition means 1, storage means 2, specification means 3 and output means 4.

The acquisition means 1 acquires values relating to a plurality of different types of physical conditions. For example, the acquisition means 1 is composed of a plurality of known measuring means, which measure as measurement data those values relating to the plurality of different types of physical conditions, such as a percent body fat, a lean body mass, a leg lean body mass, an intracellular fluid volume, an extracellular fluid volume, a gravity center sway distance, and a pulse differential count between sitting position and standing position. In the overview thereof, the acquisition means 1 comprises a first measuring main unit 11 and a second measuring main unit 21. It is to be noted that those values relating to the physical conditions may be categorized into two types: one representative of the values relating to a body constitution, which include the percent body fat, the lean body mass, the leg lean body mass, the intracellular fluid volume and the extracellular fluid volume; and the other one representative of the values relating to a physical conditioning ability, which include the gravity center sway distance and the pulse differential count between sitting position and standing position.

The first measuring main unit 11 comprises an electrode 15 for detecting a bio-impedance, a first pulse sensor 12 for detecting a pulse in a standing position, a first power switch 13 for introducing an electric power to the first measuring main unit 11 and the second measuring main unit 21, and a first communication section 14 for data communication with a second communication section 37, all of which are disposed in the exterior portion of a scale 16. The electrode 15 for detecting the bia-impedance comprises a current-carrying electrode 15a and a measuring electrode 15b. In this regard, the current-caring electrode 15a is located in a site where a toe portion of a foot of a subject is to be placed when he/she steps on the scale 16, while the measuring electrode 15b is located in a site where a heel portion of the foot of the subject is to be placed when he/she steps on the scale 16. Besides, the first pulse sensor 12 is composed of a light-emitting diode and a phototransistor and located in a site where a thumb of either foot of the subject is to be placed when he/she steps on the scale 16. Further, the first communication section 14 comprises a light-emitting diode and a phototransistor and located in a site as defined to be in a front side of the subject when he/she steps on the scale 16.

In addition, there are disposed in the interior of the scale 16 those known structural components for detecting a body weight and/or a sway of the gravity center including a plurality of weight sensors, as well as an electronic circuit board unit for mounting thereon known electronics serving for executing measurement control processing such as amplification, A/D conversion, an arithmetic operation, controlling and storing, which are required to measure a body weight, a gravity center sway, a bio-impedance and a pulse and also to determine a percent body fat, a lean body mass, a leg lean body mass, an intracellular fluid volume, an extracellular fluid volume, a gravity center sway distance and a pulse differential count between sitting position and standing position. The electrode 15 and the first pulse sensor 12 are connected to the electronic circuit board unit.

The second measuring main unit 21 comprises a second pulse sensor 22 installed in a chair 25, which detects a pulse in a sitting position. This second pulse sensor 22 comprises a light-emitting diode and a phototransistor and located in a site where a first finger of either hand of the subject is generally placed when he/she places his/her hand on an arm rest 23 of the chair 25, and said second pulse sensor 22 is connected to the electronic circuit board unit of the first measuring main unit 11 via an electric cord 24.

The storage means 2 stores, firstly, active motion disabled levels associated with the values relating to the plurality of different types of physical conditions acquired by the acquisition means 1 described above. Said active motion disabled level is indicative of an occurrence rate of a disability with respect to an active motion.

For example, the active motion disabled levels associated with the values relating to the plurality of different types of physical conditions to be stored in this storage means 2 are determined by analyzing a correlation between questions on ADL (Activities of Daily Living) indicating the level sufficient to have a independent daily life and the values for the plurality of different types of physical conditions at the time of said questioning with respect to an aged person as a subject, and denoted by an equation (1) below.

$$Y=(a \times X_1+b \times X_2 \times U_1+c \times X_3+z) \times U_2 \tag{1}$$

where, $U_1$ and $U_2$ are determined as below:

$$U_1=\{(X_6/X_4)-1.35\}/1.35 \tag{2}$$

$$\text{If } X_6 \leq 10 \text{ or } 100 \leq X_6, \text{ then } U_2= \tag{3}$$

$$\text{If } 10<X_6<100, \text{ then } U_2=1 \tag{4}$$

In this regard, respective symbols in the above equation are designated as follows:

Y: active motion disabled level,
$X_1$: percent body fat,
$X_2$: leg lean body mass or lean body mass,
$X_3$: gravity center sway distance,
$X_4$: extracellular fluid volume,
$X_5$: intracellular fluid volume,
$X_6$: pulse differential count between sitting position and standing position,
$U_1$: weighting coefficient determined from extracellular fluid volume/ the extracellular fluid volume,
$U_2$: weighting coefficient determined from the pulse differential count between sitting position and standing position, and
a, b, c, z: coefficient.

Variables included in the above-denoted equation are designated as those values relating to the plurality of different types of physical conditions acquired in the acquisition means 1, which are the percent body fat, the leg lean body mass (or lean body mass), the intracellular fluid volume, the extracellular fluid volume, the gravity center sway distance and the pulse differential count between sitting position and standing position. Those variables, in the light of the fact that many researches have found the specific relation between the ADL and the physical strength with respect to the aged person as a subject, have been chosen as the good elements representative of the values relating to the body constitution and/or the values relating to the physical conditioning ability, which may exert an important influence on the physical strength of the aged person. In this regard, since the percent body fat, the lean body mass and the leg lean body mass have connection with the muscle strength, the intracellular fluid volume and the extracellular fluid volume with the quality of the muscle, and the gravity center sway distance and the pulse differential count between sitting position and standing position with the autonomic nerves function, therefore they have been considered the factors affecting the physical strength. It is to be noted that, the intracellular fluid volume, the extracellular fluid volume and the pulse differential count between sitting position and standing position are designated as the variables used to determined the coefficients weighting the values relating to the other physical conditions. Further, in the equation (1), the $X_2$ denotes the leg lean body mass or the lean body mass, wherein preferably the leg lean body mass having stronger relevance to the leg muscle strength should be rather used, which will particularly exert an influence on the ADL, thereby improving the accuracy in determination.

The storage means 2 stores, secondly, first advice information associated with said active motion disabled levels. The first advice information associated with said active motion disabled levels, which is to be stored in this storage means 2, is designated as a type of information presented as an advice to the person to be measured, including a warning, an evocation, a reminder and a caution with respect to the result of active motion disabled levels. For example, such first advice information associated with the active motion disabled levels, as shown in FIG. 3, may be stored in the storage means 2.

The storage means 2 stores, thirdly, second advice information associated with the values relating to each individual physical condition among the plurality of different types of physical conditions acquired in the acquisition means 1 as discussed above. The second advice information associated with the values relating to each individual physical condition, which is to be stored in this storage means 2, is designated as a type of information presented as an advice to the person to be measured, including a warning, an evocation, a reminder and a caution with respect to the values relating to each individual physical condition. For example, such second advice information associated with the values relating to each individual physical condition, as shown in FIG. 4, may be stored in the storage means 2.

It is to be noted that the storage means 2 is arranged in the inside of a case 38, in the form of, for example, an electronic circuit board unit mounted on an electronic circuit board as a known electronics component serving as a storage.

The specification means 3 specifies, firstly, the active motion disabled level stored in the storage means 2, based on the values relating to the plurality of different types of physical conditions acquired in the acquisition means 1. For example, the weighting coefficients are determined by using the equations (2) through (4) on the basis of the pulse differential count between sitting position and standing position, the intracellular fluid volume and the extracellular fluid volume, each having been acquired by the acquisition means 1, and then those determined weighting coefficients as well as the percent body fat, the leg lean body mass (or the lean body mass) and the gravity center sway distance are applied to the equation (1) to determine and thus specify the active motion disabled level.

The specification means 3 further specifies, secondly, the first advice information stored in the storage means 2 based on the previously (firstly) specified active motion disabled level. To explain this in more detail, this specification is made effect by choosing the first advice information corresponding to the previously (firstly) specified active motion disabled level, out of the first advice information associated with the active motion disabled levels, as shown in FIG. 3, which has been stored in the storage means 2. For example, if the active motion disabled level "Y" is determined to be 1.5, then "Good. Hold on the current state." will be specified as the first advice information.

The specification means 3 further specifies, thirdly, the second advice information stored in the storage means 2 based on the values relating to each individual physical condition among the plurality of different types of physical conditions acquired in the acquisition means 1. To explain this in more detail, this specification is made effect by choosing the second advice information corresponding to the percent body fat, the leg leans body mass (or the lean body mass) and the gravity center sway distance, respectively, each having been acquired in the acquisition means 1, out of the second advice information associated with the values relating to each individual physical condition, as shown in FIG. 4, which has been stored in the storage means 2. For example, those pieces of second information may be specified respectively: "Appropriate percent fat of entire body. Hold on the current state." for the determined percent body fat "$X1$" greater than $S2$ but smaller than $S1$; "Quite sufficient muscle mass of leg. Hold on the current state." for the determined leg lean body mass (lean body mass) "$X2$" equal to or greater than $S3$; and "Very good body balance. Hold on the current state." for the gravity center sway distance "$X_3$" equal to or smaller than $S6$.

It is to be noted that the specification means 3 is arranged in the inside of the case 38, in the form of, for example, an electronic circuit board unit mounted on an electronic circuit board as a known electronics component serving for an arithmetic operation and/or a control.

The output means 4 outputs the active motion disabled level specified in the specification means 3. For example, the output means 4 may be display means 32 which provides a indication of the resultant values relating to a plurality of different types of physical conditions, such as the percent body fat, the leg lean fat mass (or the lean fat mass) and the gravity center sway distance and/or a graphical display of the active motion disabled level with its axis corresponding to the values relating to the plurality of different types of physical conditions, such as the percent body fat, the leg lean body mass (or the lean body mass) and the gravity center sway distance.

It is to be noted that the output means 4 is arranged in the inside of the case 38 as a known electronics component serving for an output of a result. For example, the display means 32 is arranged in the front surface of the case 38 and connected to the electronic circuit board unit inside of the case 38.

A display case section 31 comprises a second power switch 33 for introducing an electric power, a set switch 34 for setting a variety of input items, a selection switch 35 for selecting a variety of input items, and a switching switch 36 for switching a variety of input items, which are all disposed in said case 38 provided with the electronic circuit board unit and the display 32 therein. Also, the second communication section 37 for data communication with the first communication section 14 is located in a lower site of the display case section 31.

Figure 5:
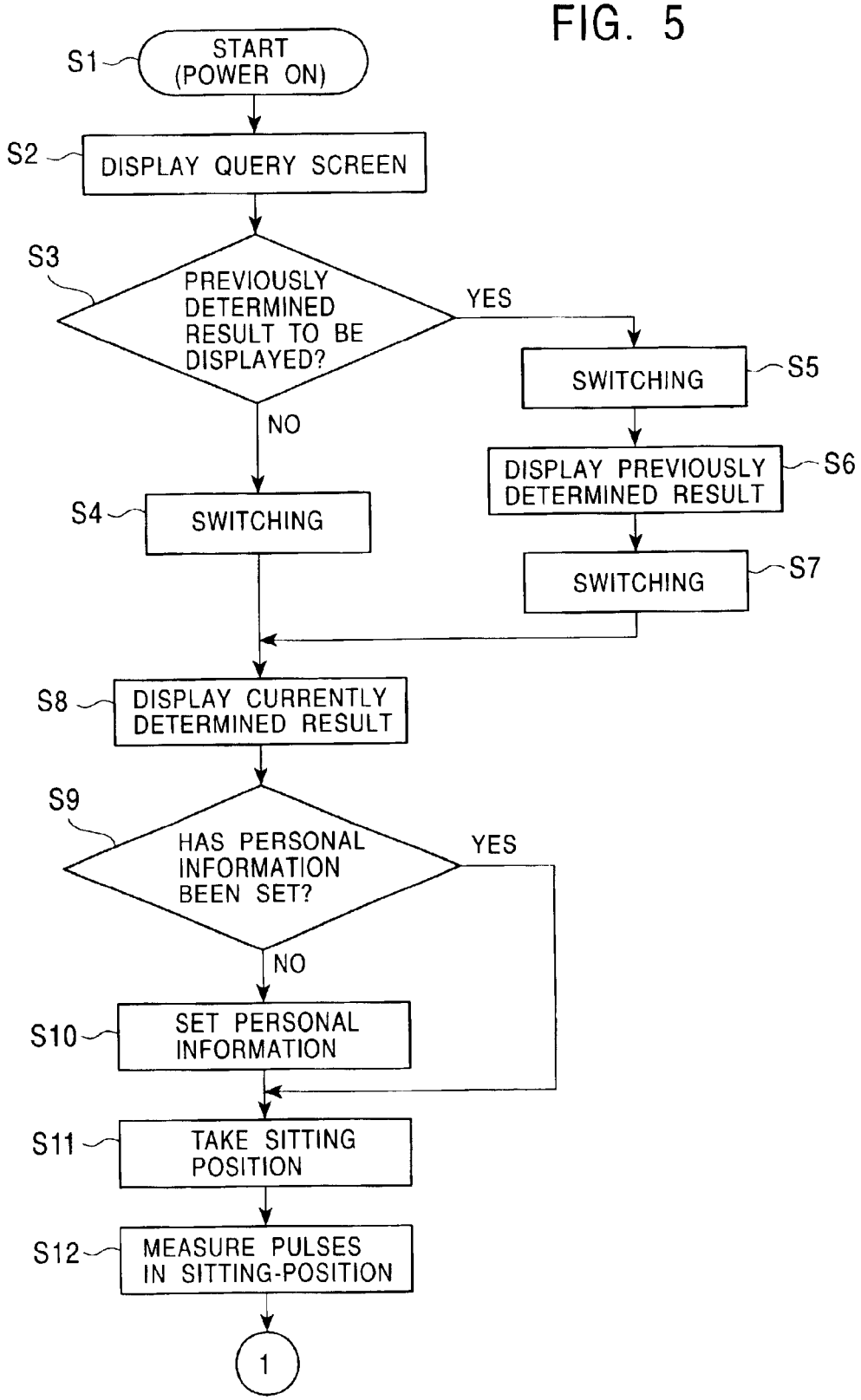
FIG. 5 is a flow chart illustrating (a first half of) a using procedure and operation of the active motion disability determining apparatus according to (the first embodiment of) the present invention.
Figure 6:
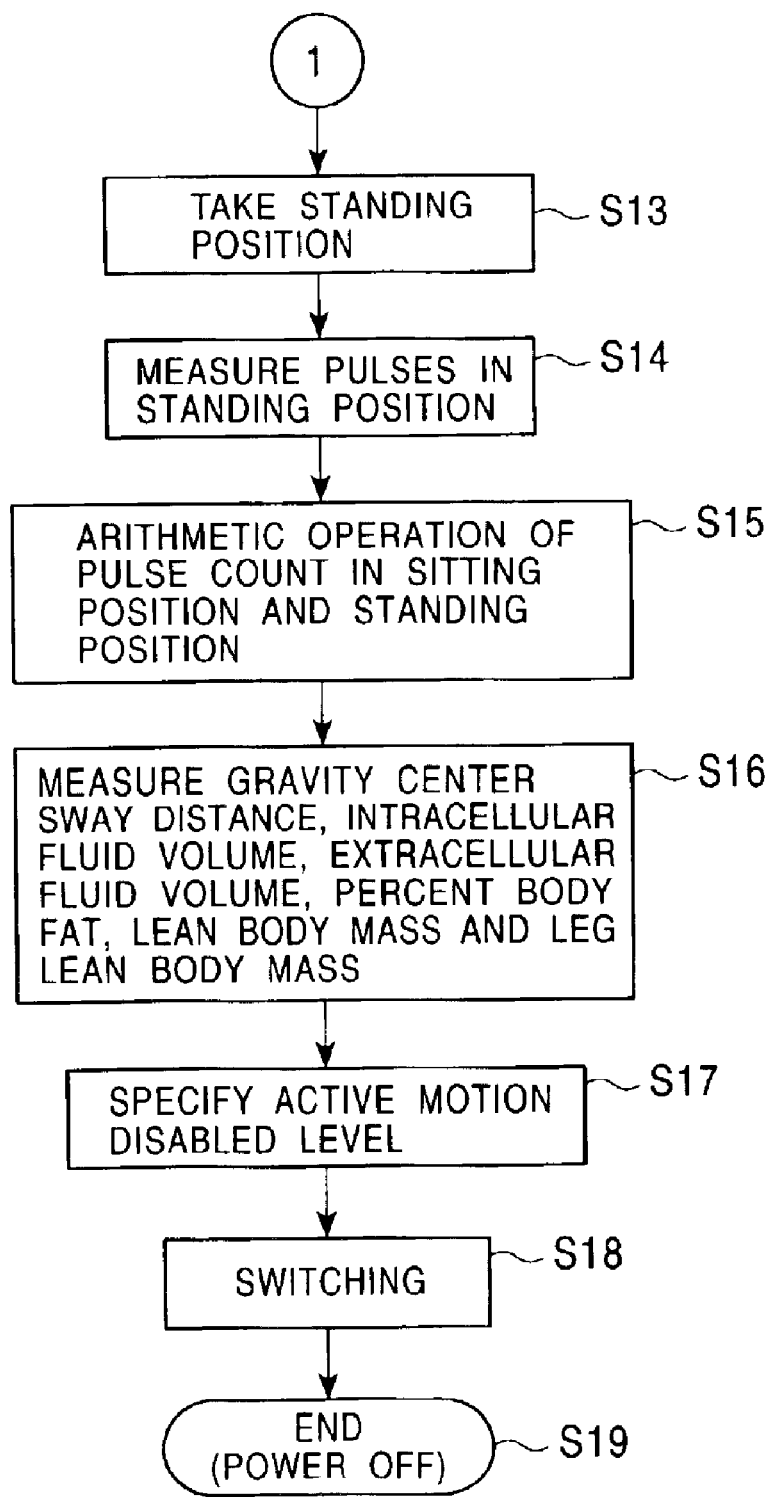
FIG. 6 is a flow chart illustrating (a second half of) the using procedure and operation of the active motion disability determining apparatus according to (the first embodiment of) the present invention.

Referring now to FIG. 5 and FIG. 6, a flow chart for illustrating a using procedures and operation of an active motion disability determining apparatus according to the present invention is shown therein. It is to be appreciated that the description is provided on the measuring main units 11, 21 and the display case section 31 collectively, rather than separately. First of all, a person to be measured presses the power switches 13, 33 disposed in the first measuring main unit 11 and the display case section 31, respectively (Step 1). Thereby the active motion disability determining apparatus is activated into an operative mode, and a query screen appears on the display means 32 of the display case section 31 requesting the person to be measured to determine whether or not a previously determined result should be indicated (Step 2).

Subsequently, the person to be measured, if he/she does not want the previously determined result to be indicated (NO in Step 3), sets a cursor to "NO" indicated on the query screen by pressing the selection switch 35, and the screen is switched accordingly as set by pressing the set switch 34 (Step 4). Through those steps, the display means 32 of the display case section 31 makes a currently determined result screen appear thereon (Step 8).

Otherwise, the person to be measured, if he/she wants the previously determined result to be indicated (YES in Step 3), sets the cursor to "YES" indicated on the query screen by pressing the selection switch 35, and the screen is switched accordingly as set by pressing the set switch 34 (Step 5). Through those steps, the display means 32 of the display case section 31 makes the previously determined result screen appear thereon (Step 6). Subsequently, to switch the display from this previously determined result screen to the currently determined result screen, the switching switch 36 is pressed thus to switch the display (Step 7).

Subsequently, the currently determined result screen indicates thereon a set of information particular to an individual, consisting of a personal number, sex, age, and height, as well as the values relating to the physical condition, consisting of the percent body fat, the leg lean body mass (or the lean body mass), the intracellular fluid volume, the extracellular fluid volume, the gravity center sway distance and the pulse differential count between sitting position and standing position, and also the active motion disabled level. Further, the active motion disabled level may be indicated in the form of graph by pressing the switching switch 36 (Step 8). In this regard, since the currently determined result screen in step 8 is in a state as before the determination, the displayed values relating to the physical condition and the display of the active motion disabled level as well as the graphical representation thereof are indicated as 0 "zero".

If the information particular to the individual has not yet set in the currently determined result screen in said step 8 (NO in Step 9), then the person to be measured sets the information particular to the individual (Step 10). To set the information particular to the individual, the set switch 34 shall be pressed to switch the cursor to the personal number field by the use of switching property in which each pressing operation of said set switch 34 can switch the cursor to respective fields of personal number, sex, age and height, in sequence. Then, the selection switch 35 is pressed to select an unregistered personal number, and the selected personal number is set by pressing the set switch 34 again. In next operation, in which the cursor is switched to the field of sex, the selection switch 35 is pressed to select the sex and then the set switch 34 is pressed to set the selected sex. In next operation, in which the cursor is switched to the field of age, the selection switch 35 is pressed to select the age and then the set switch 34 is pressed to set the selected age. In next operation, in which the cursor is switched to the field of height, the selection switch 35 is pressed to select the height and then the set switch is pressed to set the selected height.

Subsequently, if the information particular to the individual has been already set in the currently determined result screen in said Step 8 (YES in Step 9) or after Step 10, the person to be measured sits on a seat 26 of the second measuring main unit 21 (the chair 25), places his/her hand on the arm rest 23 with the first finger thereof in a position matched to the site in which the second pulse sensor 22 is located, and then the person to be measured holds on this state with his/her eyes closed (Step 11).

Subsequently, the second pulse sensor 22 detects pulses of the person to be measured during his/her sitting position, and from thus detected data, the electronic circuit board unit of the first measuring main unit determines and stores therein a sitting position pulse count (Step 12).

In the following step, the person to be measured, in the standing position, steps on the first measuring main unit 11, while positioning the first finger of either foot in alignment with the site in which the first pulse sensor 12 is located and placing respective soles of the feet across the current-carrying electrode 15a and the measuring electrodes 15b so as to contact with both sets of electrodes, and then the person to be measured holds on this standing position with his/her eyes open (Step 13).

Subsequently, the first pulse sensor 12 detects pulses of the person to be measured during his/her standing position, and from thus detected data, the electronic circuit board unit of the first measuring main unit 11 determines a standing position pulse count (Step 14), and further determines a pulse differential count between sitting position and standing position "$X_6$" indicative of a difference relative to the previously stored sitting position pulse count, which is then stored therein (Step 15).

In next operation, the weight sensor detects a body weight and a gravity center sway distance, and from thus detected data, the electronic circuit board unit of the first measuring main unit 11 determines a body weight value and a gravity center sway distance $X_3$, which are then stored therein. Subsequently, the electrode 15 detects the bio-impedances corresponding to a first, a second and a third frequencies, respectively, and then the electronic circuit board unit of the first measuring main unit 11 processes these bio-impedance values in conjunction with the previously stored body weight value and the information particular to the individual (age, height), to determine an extracellular fluid volume "$X_4$", an intracellular fluid volume "$X_5$", a percent body fat "$X_1$" and a leg lean body mass (or a lean body mass) "$X_2$", respectively, which are then stores therein. It is to be appreciated that, for example, the percent body fat, $X_1$, may be calculated by the following equation (5), and the leg lean body mass (or the lean body mass), $X_2$, may be calculated by the following equation (6) respectively.

$$X_1 = m \times H^2 / W \times Z + n \times 1/Z + y \qquad (5)$$

$$X_2 = p \times H^2 / Z + q \times Z + r \times A + t \qquad (6)$$

where, respective symbols are designated as follows:

$X_1$: percent body fat,
$X_2$: leg lean body mass (or lean body mass)
H: height
W: weight
Z: bio-impedance
A: age
m, n, y, p, q, r, t: coefficient.

Further, the extracellular fluid volume and the intracellular fluid volume may be determined by such a way as disclosed in U.S. Pat. No. 6,532,384, the entire disclosure of which is incorporated herein by reference (Step 16).

Subsequently, respective measured data determined in Step 15 and Step 16, consisting of the pulse differential count between sitting position and standing position, the gravity center sway distance, the extracellular fluid volume, the intracellular fluid volume, the percent body fat and the leg lean body mass (or the lean body mass), are transmitted from the first communication section 14 of the first measuring main unit 11 to the second communication section 37 of the display box section and then stored in the electronic circuit board unit of the display case section 31. In accordance with the equations (1), (2), (3) and (4), the electronic circuit board unit of the display case section 31, in turn, determines and stores an active motion disabled level (Step 17).

In next operation, the currently determined result screen containing the measured data as described above is made appear on the display means 32, as shown in FIG. 7. Further, by pressing the switching switch 36, the display is switched and indicates such a graphical display in conjunction with an advice as shown in FIG. 8 (Step 18).

Figures 8, 9:
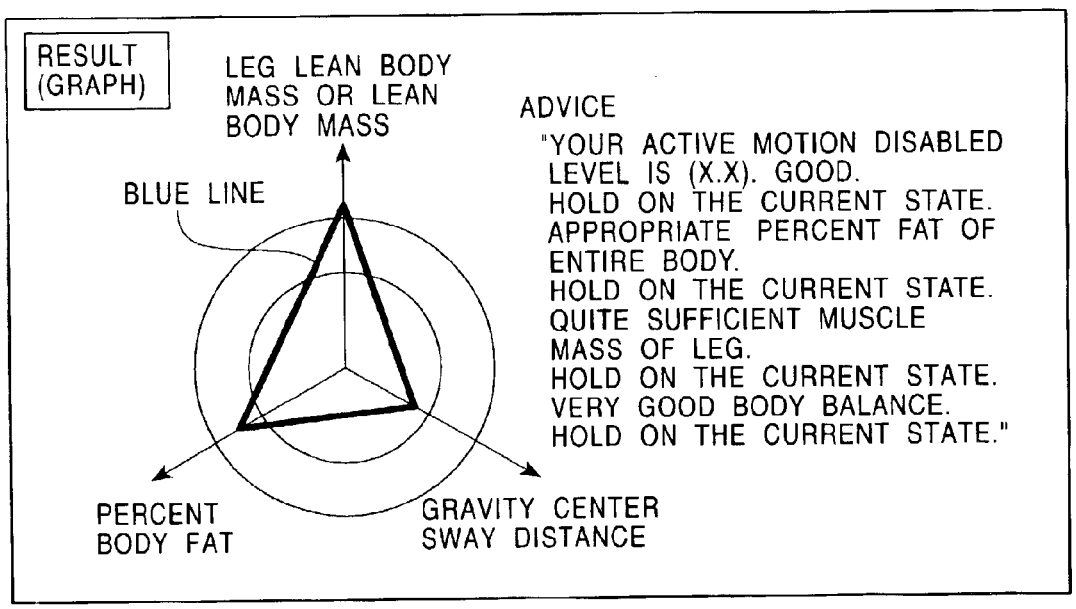
FIG. 8 is a diagram illustrating an example of an indication (graph, advice) on the screen for a currently determined result.
FIG. 9 shows an example of colors associated with the active motion disabled levels.

This graphical display shows the lines connecting to one another those points corresponding to the measured data on the axes indicating the percent body fat, the leg lean body mass (or he lean body mass) and the gravity center sway distance, respectively, in which the lines are drawn in different colors depending on the active motion disabled levels as designated in FIG. 9.

Further, the advice indication is displayed in the form of combination of: the one selected as the first advice information corresponding to the active motion disabled level specified as the measurement data from such a first advice information associated with the active motion disabled levels as shown in FIG. 3, which has been stored in the electronic circuit board unit of the second measuring main unit 21; and the one selected as the second advice information corresponding to the percent body fat, the leg lean body mass (or the lean body mass) and the gravity center sway distance acquired as the measurement data from such a second advice information associated with the values relating to each individual physical conditions as shown in FIG. 4. It is to be noted that FIG. 8 shows an example of display of the advice information specified for the determined active motion disabled level Y equal to or greater than 1 but smaller than 2, the percent body fat $X_1$ greater than S2 but smaller than S1, the leg lean body mass $X_2$ equal to or greater than S3, and the gravity center sway distance $X_3$ not greater than S6.

In the operation following to the Step 18, the power switches 13, 33 are turned off, thereby ending the series of procedures (Step 19).

As described above, since the active motion disability determining apparatus, which is one type of the daily-life disability related physical information determining apparatus according to the first embodiment of the present invention, measures those values relating to a plurality of different types of physical conditions, such as the percent body fat, the lean body mass, the leg lean body mass, the intracellular fluid volume, the extracellular fluid volume, the gravity center sway distance, and the pulse differential count between sitting position and standing position, and based on those values, specifies in the specification means 3 thereof the active motion disabled level stored in the storage means 2 with respect to the aged person as a subject, as well as the first and the second advice information, and further displays in the display means 32 thereof the specified data, therefore the determination on the active motion disabled level and/or the advice information can be obtained automatically, providing a high utility value as well as an easily perceivable result display.

It is to be noted that although in the first embodiment described above, the acquisition means 1 has been defined as measuring means, in an alternative embodiment, the values relating to the plurality of different types of physical conditions may be acquired through input means for inputting those values. For example, the display case section 31 may be provided with a switch for inputting the percent body fat, the lean body mass, the leg lean body mass, the gravity center sway distance, the intracellular fluid volume, the extracellular fluid volume, and the pulse differential count between sitting position and standing position, respectively, in which the percent body fat, the lean body mass, the leg lean body mass, the gravity point disturbed distance, the intracellular fluid volume, the extracellular fluid volume, and the pulse differential count between sitting position and standing position, which have been known in advance via separate measuring equipment may be input through this switch.

Further, although in the above-described embodiment, the values relating to a plurality of different types of physical conditions have been designated as the percent body fat, the lean body mass, the leg lean body mass, the gravity center sway distance, the intracellular fluid volume, the extracellular fluid volume, and the pulse differential count between sitting position and standing position, those values relating to the body fat, the lean body, the leg lean body, the gravity center sway, the intracellular fluid, the extracellular fluid, and the pulse differential between sitting position and standing position may also be used to carry out the present invention. For example, the percent body fat may be replaced with a body fat mass, the lean body mass may be replaced with a percent lean body, the leg lean body mass may be replaced with a percent leg lean body, and the gravity center sway distance may be replace with a gravity center sweep area. Further, if there are given at least two of them, the present invention may be similarly carried out. It is to be noted that those values relating to the physical conditions are the ones which can be easily measured with only a small load applied to the body. Yet further, the values are not limited to those designated above but values relating to a body constitution and/or physical conditioning ability, which may exert affections on the physical strength, including a muscle strength, an instantaneously exertive power, a muscle staying power, an entire body staying power, equilibration, agility and flexibility, may also be used to carry out the present invention. For example, the value relating to the body constitution may be a value relating to the muscle, including an entire body muscle mass or a percent entire body muscle and/or a leg muscle mass or a percent leg muscle. Further, although in the above description for the embodiment of the present invention, such a factor as causing a deterioration in the leg strength has been employed as the value relating to the physical condition, alternatively another factor causing a deterioration in the hand strength, such as an arm lean body mass or an arm muscle mass, may be used as the value relating to the physical condition.

Further, although the active motion disabled level has been designated as a disabled level relating to the ADL, other type of disabled level may be used so far as it is indicative of the occurrence rate of the disability relating to the active motion. Yet further, although the aged person has been placed as the subject, an individual in other age groups or in every one of age groups, or either one of female individual or male individual may be the subject to be measured.

Further, although in the above embodiment, the storage means 2 has stored the equation (1) and the specification means 3 has specified the active motion disabled level in an arithmetic operation by substituting the values relating to a plurality of different types of physical conditions into proper terms in the equation (1), the storage means 2 may store such a corresponding relation table between an active motion disabled level and a plurality of different types of physical conditions as shown in FIG. 10, so that the specification means 3 may specify the active motion disabled level by selecting the active motion disabled level corresponding to the values relating to the plurality of different types of physical conditions, which has acquired in the acquisition means 1. For example, for given values of the percent body fat of 26, the leg lean body mass (or the lean body mass) of 5 and the gravity center sway distance of 25, the active motion disabled level of Y3 may be specified.

Figure 11:
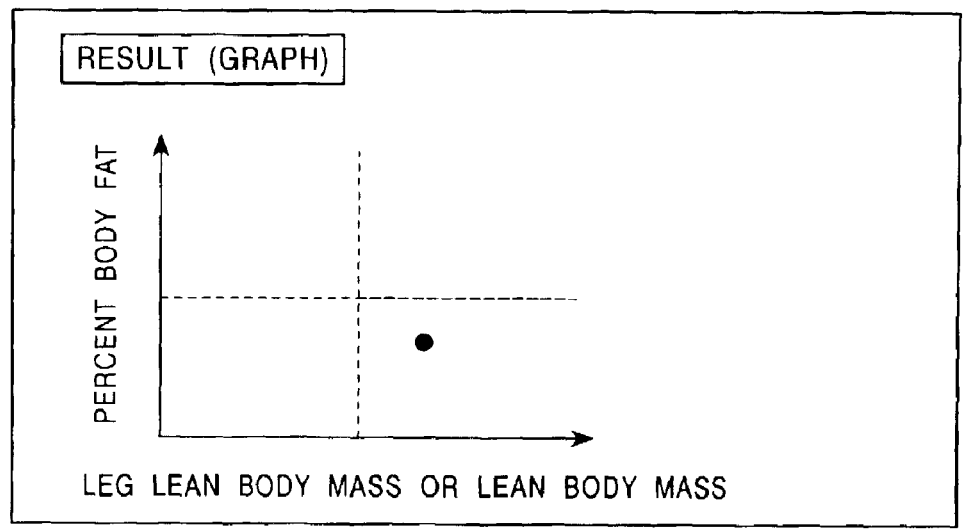
FIG. 11 is a diagram illustrating an example of an indication (graph) on the screen for a currently determined result.

Further, although in the above embodiment, the display means 32 has provided a graphical representation of the active motion disabled level in a manner that the points corresponding to the data of respective measurements on the three of graph axes indicative of the percent body fat, the leg lean body mass (or the lean body mass) and the gravity center sway distance are connected to one another with the lines drawn in the different colors depending on the active motion disabled levels, the active motion disabled level may be displayed in other forms of graphical representation, such as one shown in FIG. 11, in which a location on which two lines drawn vertically from points corresponding to the data of respective measurements on the two axes of the graph indicative of the percent body fat and the leg lean body mass (or the lean body mass) are crossed to each other is indicated in a color associated with the active motion disabled level thus to provide one type of graphical representation of the active motion disabled level. In an alternative embodiment, the active motion disabled level may be provided in the graphical representation within a field segmented by a dotted line in association with each active motion disabled level. As discussed above, providing the graphical representation of the active motion disabled level by associating said active motion disabled level with the graph axis indicative of the value relating to each individual physical condition among the values relating to the plurality of different types of physical conditions may facilitate the grasping of the relation between the value relating to each individual physical condition among the values relating to the plurality of different types of physical conditions and the active motion disabled level.

Secondly, as a second embodiment of the present invention, a daily-life disability related physical information determining apparatus will be described in detail, which has an aspect in which physical information on a physical strength related phase of the daily-life disability is determined by stages based on a value relating to a physical condition as well as secondary physical information.

Figure 12:
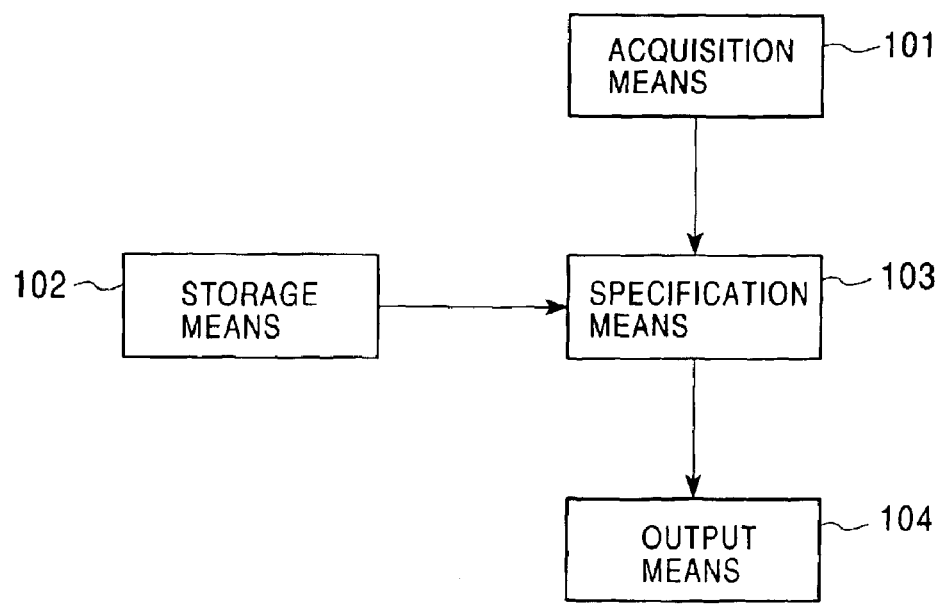
FIG. 12 is a block diagram illustrating a configuration of a daily-life disability related physical information determining apparatus according to (a second embodiment of) the present invention.
Figure 13:
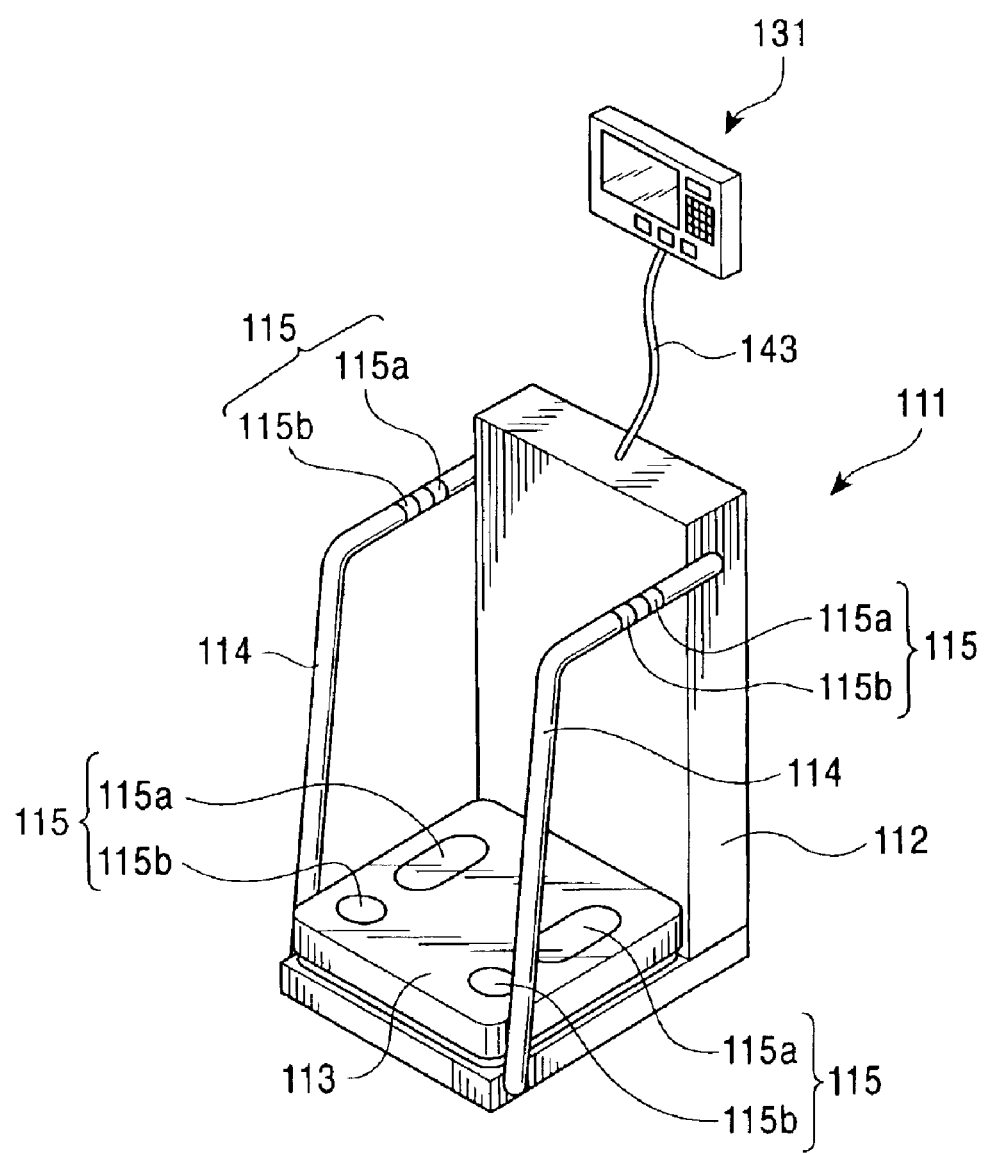
FIG. 13 is an overview of a daily-life disability related physical information determining apparatus according to the present invention.
Figure 14:
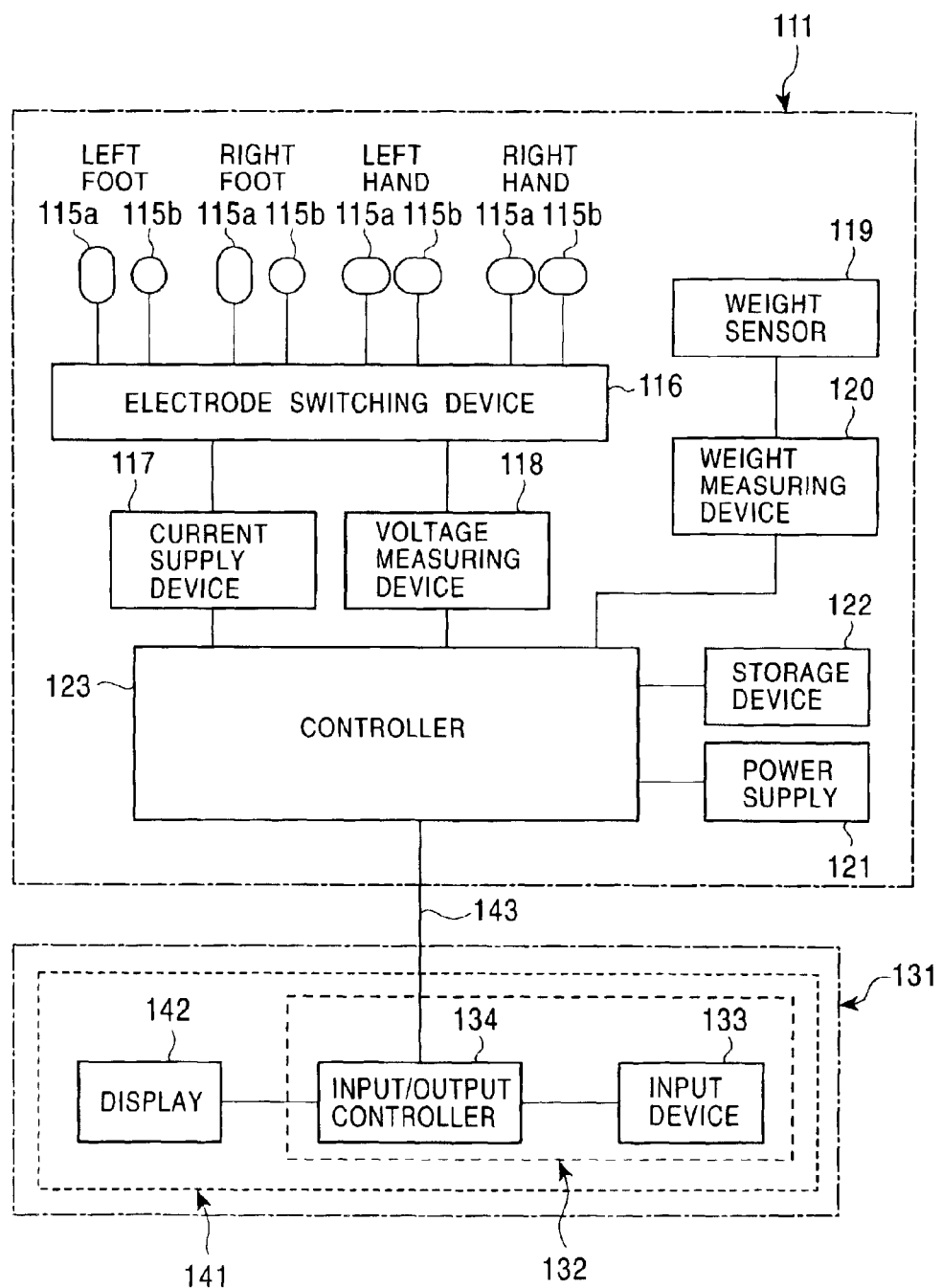
FIG. 14 is a detailed block diagram illustrating a configuration in a specific structure of the daily-life disability related physical information determining apparatus according to (the second embodiment of) the present invention.
Figure 15:
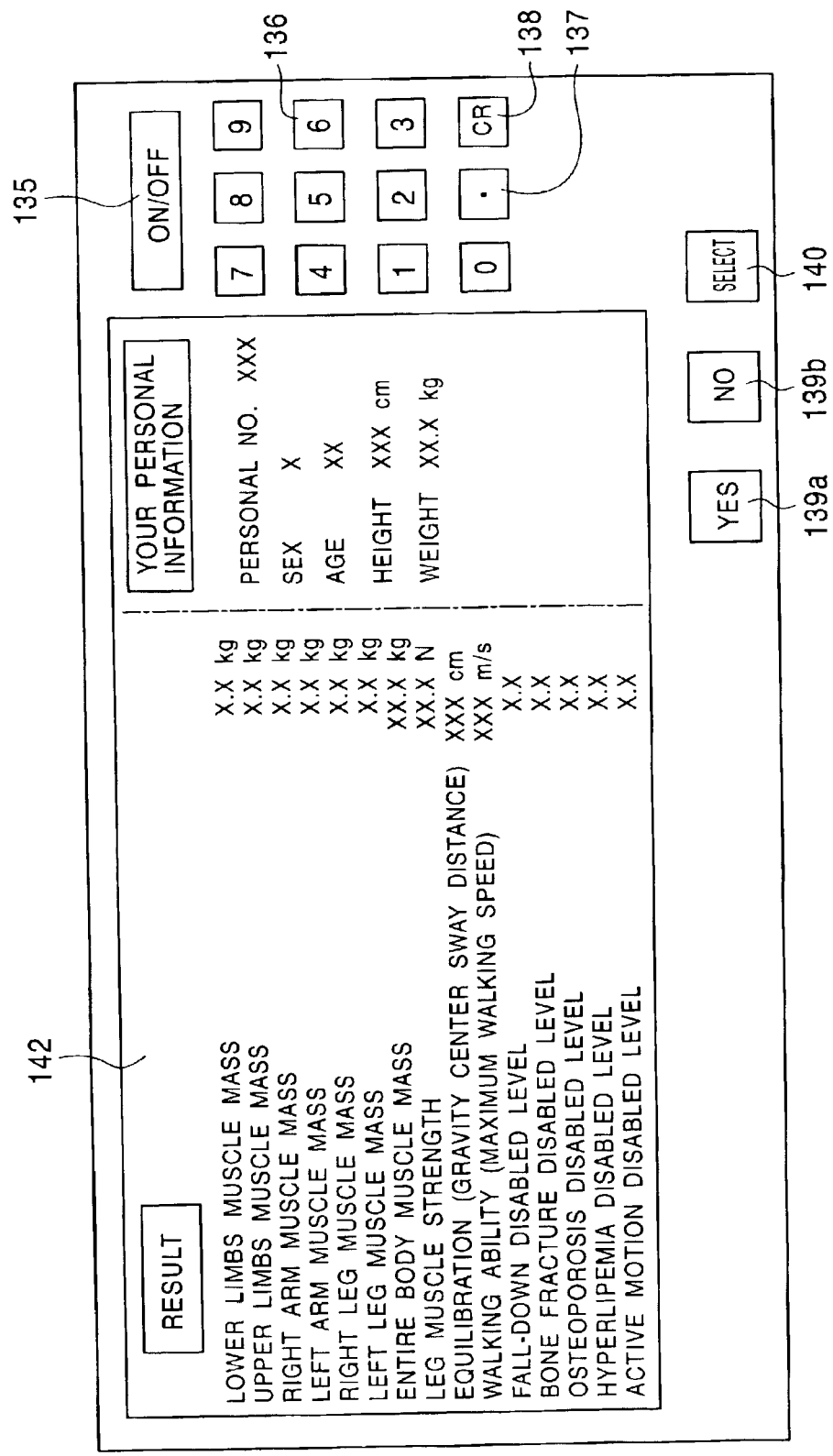
FIG. 15 is a front view of a display case section of the daily-life disability related physical information determining apparatus according to (the second embodiment of) the present invention.

To begin with, a configuration of a daily-life disability related physical information determining apparatus according to the present invention is shown in FIG. 12 in a form of block diagram, and an overview thereof is shown in FIG. 13, while a configuration in its specific structure is shown in FIG. 14 in a form of detailed block diagram, and a front elevation view of a display case section thereof is shown in FIG. 15, respectively. The daily-life disability related physical information determining apparatus according to the second embodiment of the present invention comprises acquisition means 101, storage means 102, specification means 103 and output means 104.

The acquisition means 101 acquires the value relating to the physical condition as well as the secondary physical information. For example, the acquisition means 101 may comprise: a measuring main unit 111 for measuring a muscle mass of an entire body and also of each site of the body as the values relating to the physical condition as well as a body weight as the secondary physical information; and input means 132 for inputting a height, an age and a sex as the secondary physical information. It is to be noted that the muscle mass may be categorized into a kind of value relating to a body constitution among the values relating to the physical condition.

In this regard, the measuring main unit 111 includes a L-shaped base structure 112, a measuring platform 113 and a measuring hand rail 114, which all together define a general contour of the apparatus, and on or in those components are arranged or installed many elements of the apparatus, including an electrode 115 for detecting a bio-impedance, an electrode switching device 116 for switching connections in the set of those electrodes 115, a current supply device 117 for supplying a current specifically to a current-carrying electrode 115a in the set of electrodes 115 for introducing the electricity to a person to be measured, a voltage measuring device 118 for measuring the bio-impedance specifically from a measuring electrode 115b in the set of electrodes 115 for detecting a potential difference occurring in the person to be measured, a weight sensor 119 for detecting a weight signal, a weight measuring device 120 for measuring a weight from the weight signal detected by said weight sensor 119, a power supply 121 for supplying an electric power to respective sections of the apparatus, a storage device 122 for storing an arithmetic expression to be used in determining the value relating to the physical condition, data for respective operations and so on, and a controller 123 for controlling a variety of arithmetic operations for the value relating to the physical condition or the like and the operations in respective sections of the apparatus.

It is to be noted that the current-carrying electrodes 115a are located, respectively, in a site on the measuring platform 113 where a toe side of a foot of the person to be measured is placed when he/she steps on the measuring platform 113 and also in a site on the measuring hand rail 114, to which a palm (in the side of a thumb) of a hand of the person to be measured comes into contact when he/she steps on the measuring platform 113 and grips the measuring hand rail 114. Further, the measuring electrodes 115b are located, respectively, in a site on the measuring platform 113 where a heel side of the foot of the person to be measured is placed when he/she steps on the measuring platform 113 and also in a site on the measuring hand rail 114, to which the palm (in the side of a little finger) of the hand of the person to be measured comes into contact, when he/she steps on the measuring platform 113 and grips the measuring hand rail 114. Besides, respective sections such as the weight sensor 119 other than the electrodes 115 may be accommodated inside of the measuring platform 113.

Besides, the input means 132 is composed of an input/output controller 134 and an input device 133, and located in the display case section 131. It is to be appreciated that this input device 133 comprises a power switch 135, a ten key 136, a comma key 137, a clear key 138, a confirmation switch 139a, 139b and a selection switch 140. The controller 123 and the input/output controller 134 are interconnected by using an electric cord 143.

The storage means 102 stores, firstly, physical information on a physical strength related phase of a daily-life disability associated with the value relating to the physical condition and the secondary physical information acquired by the above-described acquisition means 101. For example, the storage means 102 may comprise a storage device 122 for storing the following equations: the equations (7) through (9), in which a leg muscle strength, an equilibration (for example, represented by a gravity center sway distance or a gravity center sweep area or the like) and a fall-down disabled level (indicative of an occurrence rate of a potential disability due to falling down), each given as the physical information on the physical strength related phase of the daily-life disability for the aged person placed as the subject, are individually correlated with the leg muscle mass as well as the height, weight, age and sex, given as the values relating to the physical condition; and the equations (10) through (12), in which a bone fracture disabled level (indicative of the occurrence rate of a potential disability due to the bone fracture), an osteoporosis disabled level (indicative of the occurrence rate of a potential disability due to the osteoporosis) and a hyperlipemia disabled level (indicative of the occurrence rate of a potential disability due to the hyperlipemia), each given as the physical information on the physical strength related phase of the daily-life disability for the aged person placed as the subject, are individually correlated with the entire body muscle mass as well as the height, weight, age and sex, given as the values relating to the physical condition. It is to be noted that the storage device 122 serving as the storage means 102 is shared with the storage device 122 serving as the acquisition means 101. Further, the leg muscle and/or the equilibration are categorized into the values relating to specifically a basic physical strength among the physical information on the physical strength related phase of the daily-life disability, and the fall-down disabled level and/or the bone fracture disabled level and/or the osteoporosis disabled level and/or the hyperlipemia disabled level are categorized into the values relating to the daily-life disability.

The equations (7) through (12) are expressed as follows:

$$L_1 = k_1 \times X_{11} + s_1 \times H + u_1 \times W + v_1 \times A + w_1 \times S + d_1 \quad (7)$$

$$L_2 = k_2 \times X_{11} + s_2 \times H + u_2 \times W + v_2 \times A + w_2 \times S + d_2 \quad (8)$$

$$L_3 = k_3 \times X_{11} + s_3 \times H + u_3 \times W + v_3 \times A + w_3 \times S + d_3 \quad (9)$$

$$L_4 = k_4 \times X_{12} + s_4 \times H + u_4 \times W + v_4 \times A + w_4 \times S + d_4 \quad (10)$$

$$L_5 = k_5 \times X_{12} + s_5 \times H + u_5 \times W + v_5 \times A + w_5 \times S + d_5 \quad (11)$$

$$L_6 = k_6 \times X_{12} + s_6 \times H + u_6 \times W + v_6 \times A + w_6 \times S + d_6 \quad (12)$$

where, respective symbols in the above equations are designated as follows:

$L_1$: leg muscle strength;
$L_2$: equilibration;
$L_3$: fall-down disabled level;
$L_4$: bone fracture disabled level;
$L_5$: osteoporosis disabled level;
$L_6$: hyperlipemia disabled level;
$X_{11}$: leg muscle mass;
$X_{12}$: entire body muscle mass;
H: height;
W: weight;
A: age;
S: sex; and
$k_1$–$k_6$, $s_1$–$s_6$, $u_1$–$u_6$, $v_1$–$v_6$, $w_1$–$w_6$, $d_1$–$d_6$: coefficient.

It is to be appreciated that in the above equations, each of the physical strengths is expressed, based on the data provided by many researches, as a function of respective variables relating to the physical condition with weighting factors applied thereto which have been determined in dependence on the degree of correlation to respective physical strength.

Further, the storage means 102 stores, secondly, another physical information on the physical strength related phase of the daily-life disability associated with previous physical information on the physical strength related phase of the daily-life disability as well as the secondary physical information. For example, the storage device 122 stores, in addition to what has been stored as described above, the following equations (13) and (14), in which a walking ability (represented by, for example, a maximum walking speed, a free (ordinary) walking speed, a length of step, a variation in step and so on) and an active motion disabled level (indicative of the occurrence rate of a potential disability with respect to the active motion), each given as another physical information on the physical strength related phase of the daily-life disability for the aged person placed as the subject, are individually correlated with the leg muscle strength and the equilibration, given as the previous physical information on the physical strength related phase of the daily-life disability. It is to be appreciated that the walking ability is categorized into the value relating to a motive ability among the physical information on the physical strength related phase of the daily-life disability, and the active motion disabled level is categorized into the value relating to a daily-life disability among the physical information on the physical strength related phase of the daily-life disability.

The equation (13) and (14) are expressed as follows:

$$L_7 = x_1 \times L_1 + e_1 \times L_2 + s_7 \times H + u_7 \times W + v_7 \times A + w_7 \times S + d_7 \quad (13)$$

$$L_8 = x_2 \times L_1 + e_2 \times L_2 + s_8 \times H + u_8 \times W + v_8 \times A + w_8 \times S + d_8 \quad (14).$$

where, respective symbols in the above equations are designated as follows:

$L_7$: walking ability;
$L_8$: active motion disabled level;
$L_1$: leg muscle strength;
$L_2$: equilibration;
H: height;
W: weight;
A: age;
S: sex; and
$x_1$, $x_2$, $e_1$, $e_2$, $s_7$, $s_8$, $u_7$, $u_8$, $v_7$, $v_8$, $w_7$, $w_8$, $d_7$, $d_8$: coefficient.

It is to be appreciated that in the above equations, the walking ability and the active motion disabled level are expressed as a function of the leg muscle strength, the equilibration and other factors with weighting factors applied thereto which have been determined in dependence on the degree of correlation thereto.

The specification means 103 specifies, firstly, the physical information on the physical strength related phase of the daily-life disability stored in the storage means 102 based on the value relating to the physical condition and the secondary physical information acquired by the above-described acquisition means 101. For example, the specification means 103 may comprise the controller 123 in which, the entire body muscle mass, the leg muscle mass among the muscle masses of respective sites of the body as well as the body weight measured by the measuring main unit 111 and the height, age and sex input by the input means 132 are applied to the equations (7) through (12) to determine the leg muscle strength, the equilibration, the fall-down disabled level, the bone fracture disabled level, the osteoporosis disabled level, and the hyperlipemia disabled level, thereby specifying the physical information.

The specification means 103 specifies, secondly, another physical information on the physical strength related phase of the daily-life disability associated with said specified physical information on the physical strength related phase of the daily-life disability and said secondary physical information acquired by said acquisition means, said specified physical information having been stored in the storage means 102 based on the previously specified physical information on the physical strength related phase of the daily-life disability as well as the secondary physical information acquired by said acquisition means. For example, the controller 123 may further apply such items to the equations (13) and (14), as the leg muscle strength and the equilibration specified from the equations (7) and (8) as well as the body weight measured by the measuring main unit 111 and the height, the age and the sex input by the input means 132, thus to determine the walking ability and the active motion disabled level, thereby further specifying the another physical information. It is to be noted that the controller 123 serving as the specification means 103 is shared with the controller 123 serving as the acquisition means 101.

The output means 104 outputs the physical information on the physical strength related phase of the daily-life disability specified by the specification means 103. It is to be appreciated that this output means 104 also outputs the value relating to the body constitution and/or the secondary physical information acquired by the acquisition means 101. For example, the output means 104 may comprise display means 141 for providing an indication of such items in the form of characters or a graph as: the sex, the age, the height and the body weight as the secondary physical information; the muscle mass in respective sites of the body and the entire body muscle mass as the values relating to the body constitution; and the leg muscle strength, the equilibration, the fall-down disabled level, the bone fracture disabled level, the osteoporosis disabled level, the hyperlipemia disabled level, the walking ability and the active motion disabled level as the physical information on the physical strength related phase of the daily-life disability. This display means 141 is made up of an input/output controller 134 and a display 142, and arranged in the display case section 131. The display 142 may indicate thereon the results in such forms as shown in FIGS. 15 through 18.

Figure 16:
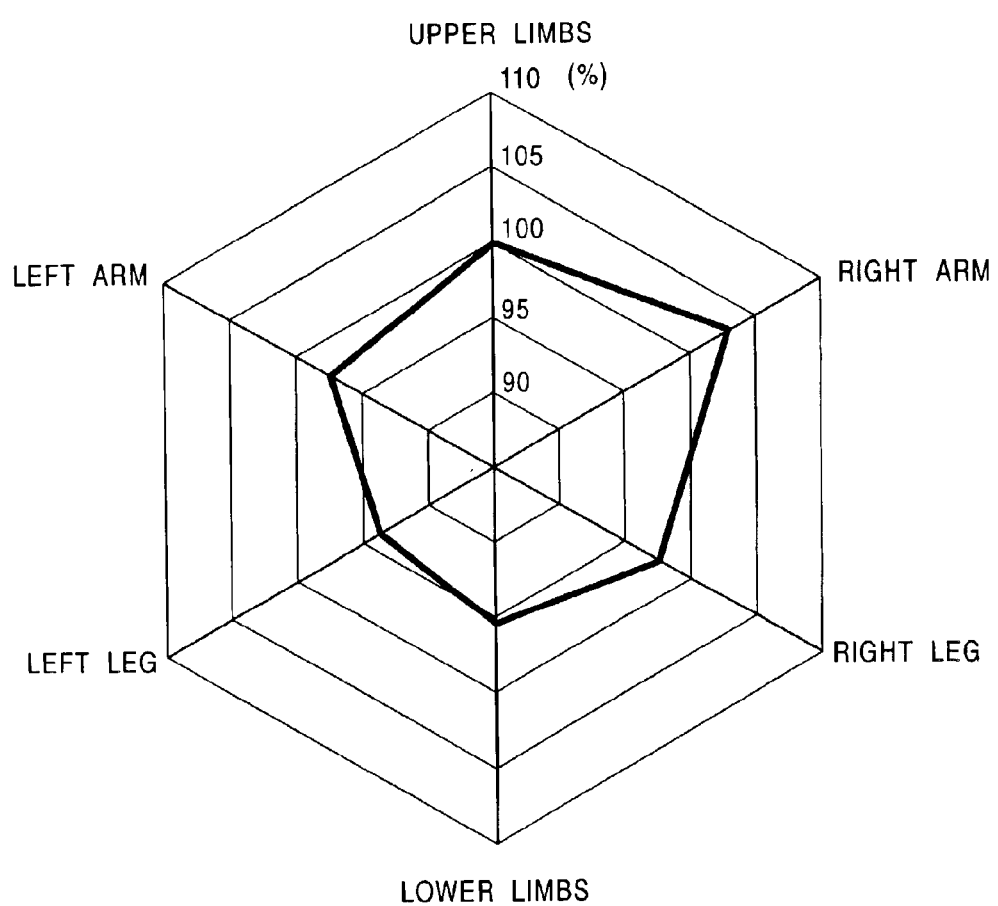
FIG. 16 shows an example of a graphical display.
Figure 17:
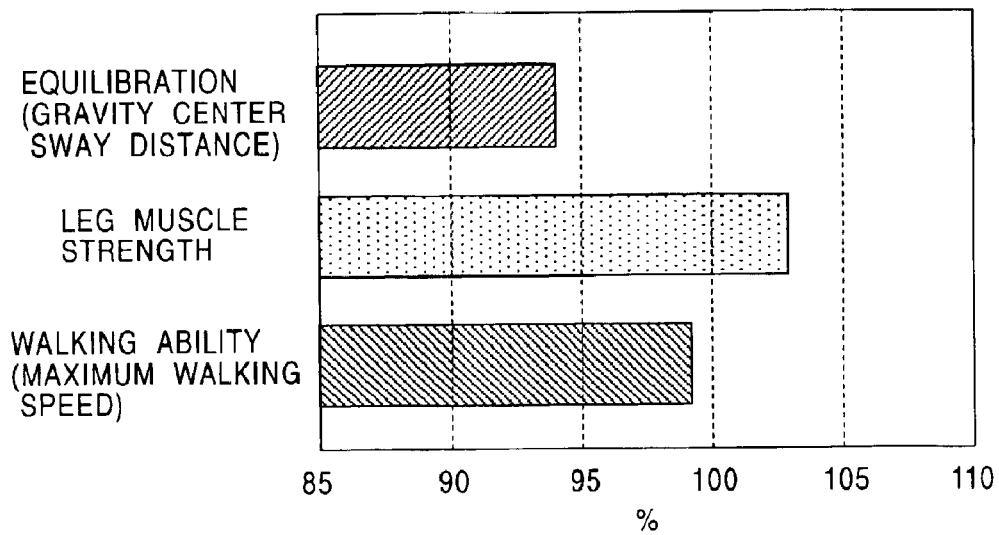
FIG. 17 shows another example of a graphical display.
Figure 18:
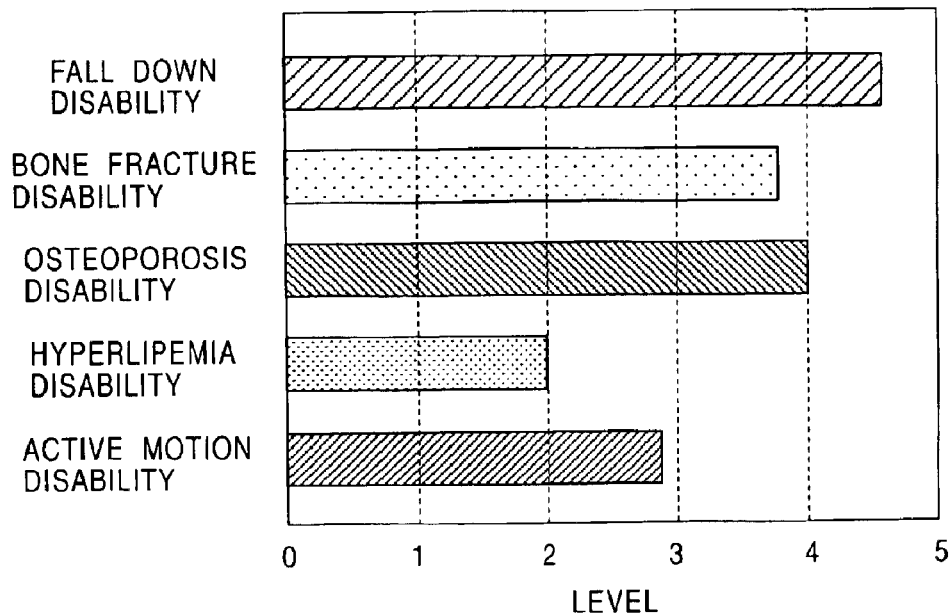
FIG. 18 shows another example of a graphical display.

The graphical representations of FIGS. 16 through 18 will now be described. FIG. 16 shows a graphical representation of the muscle masses in respective sites in a body, in which respective radial axes are assigned to respective muscle masses and graduated appropriately on the basis of the averaged muscle mass in respective sites of the body (upper limbs, lower limbs, left arm, right arm, left leg, right leg) in a group of individuals having the same age, sex and body build (height and body weight) taken as 100 in percentages, wherein those points on respective axes specifically corresponding to the subject are connected to each other thus to produce the graphical representation. FIG. 17 shows another graphical representation of the leg muscle strength, the equilibration and the walking ability in the form of bar graph, in which the axis indicative of the variation is graduated appropriately on the basis of the averaged leg muscle strength, the equilibration and the walking ability in the group of individuals having the same age, sex and body build (height and weight) taken as 100 in percentages thus to produce the graphical representation. According to FIGS. 16 and 17, the differences as compared to the group of individuals having the same age, sex and body build (height and weight) can be observed at a glance. FIG. 18 shows still another graphical representation of the occurrence rates of respective disabilities in the form of bar graph, in which the axis indicative of the variation is graduated appropriately so as to show the disabled levels representing the occurrence rates of the fall-down, the bone fracture, the osteoporosis, the hyperlipemia and the active motional disabilities, respectively.

Figure 19:
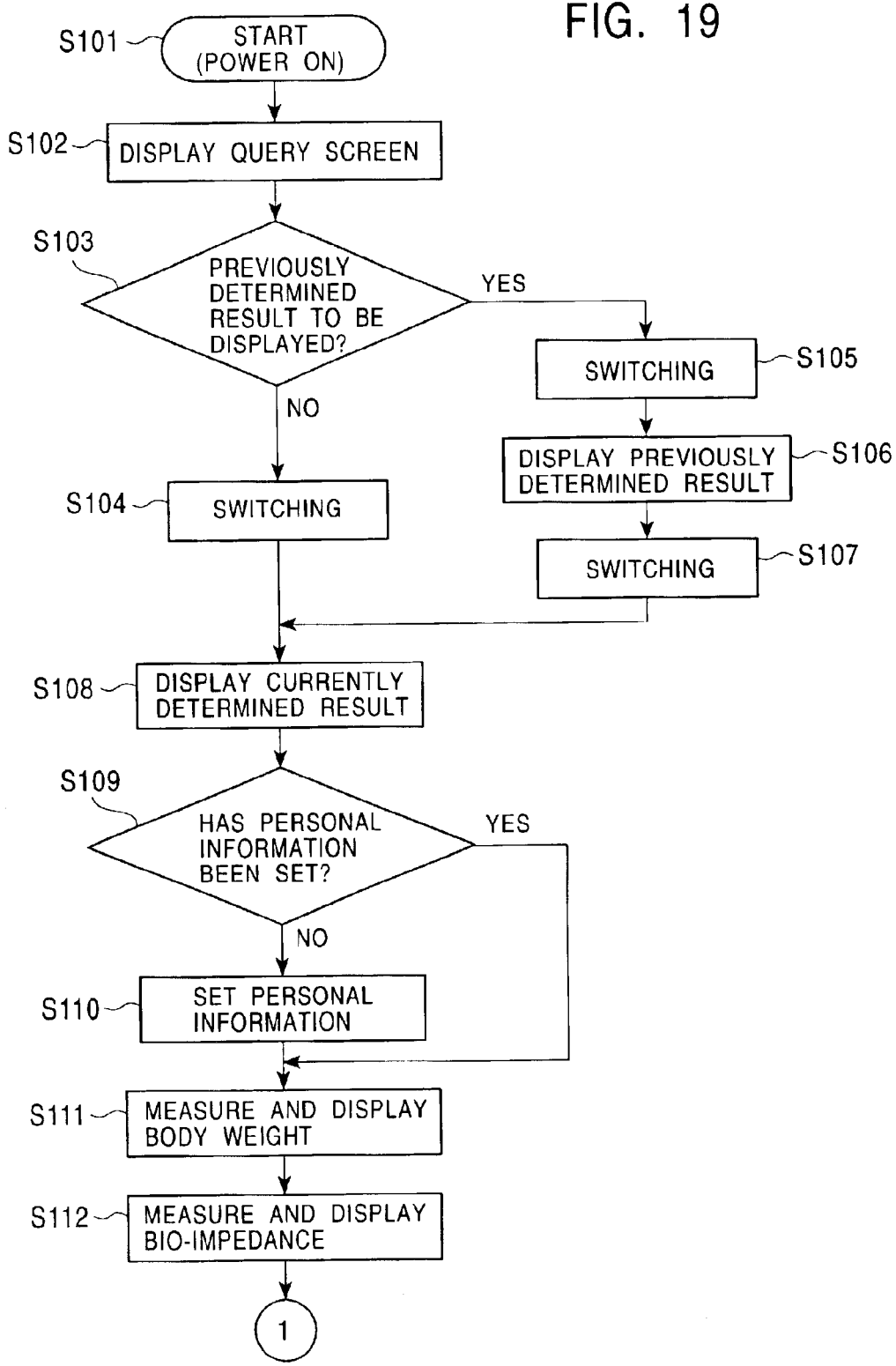
FIG. 19 is a flow chart illustrating (a first half of) a using procedure and operation of the daily-life disability related physical determining apparatus according to (the second embodiment of) the present invention.
Figure 20:
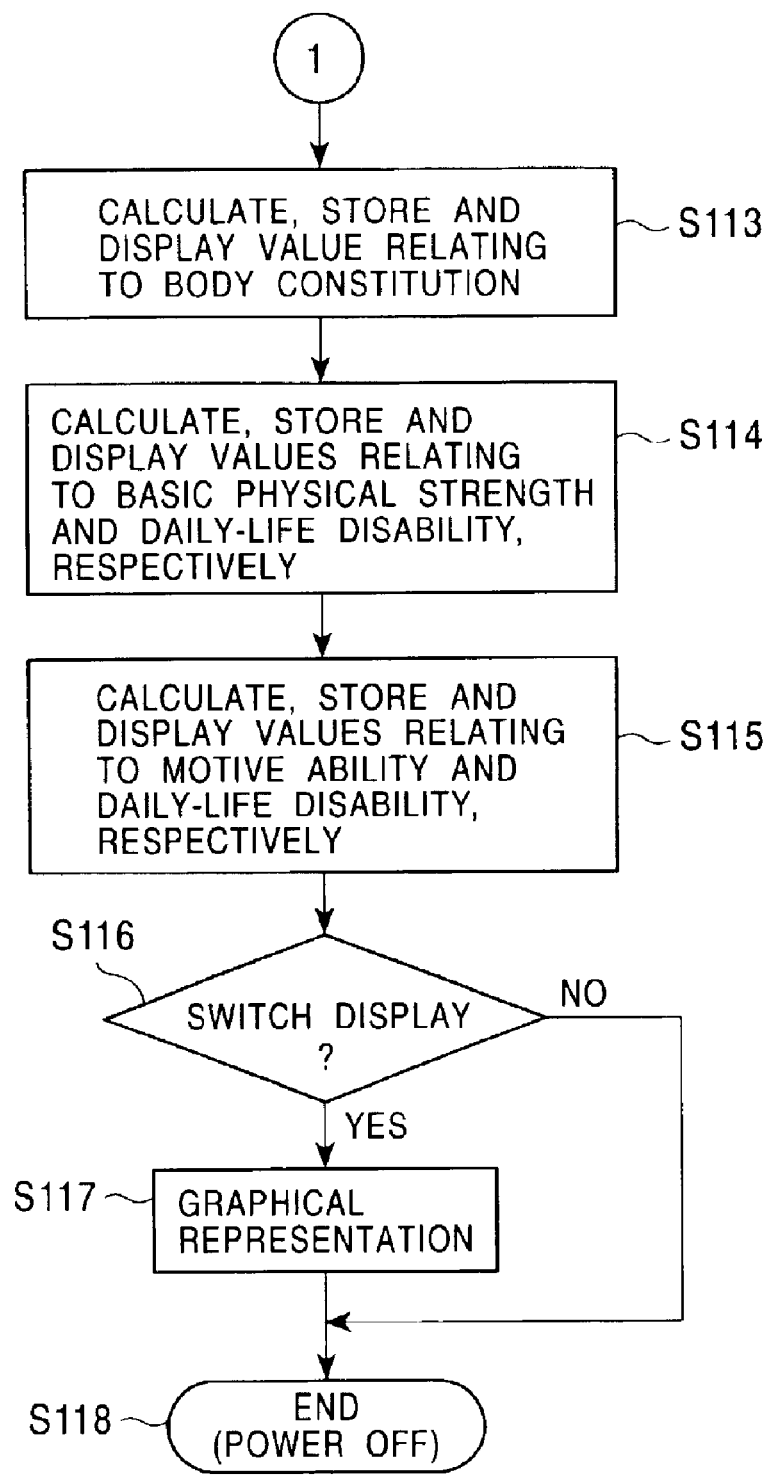
FIG. 20 is a flow chart illustrating (a second half of) a using procedure and operation of the daily-life disability related physical determining apparatus according to (the second embodiment of) the present invention.

Referring now to FIGS. 19 and 20, the using procedure and operation of the daily-life disability related physical information determining apparatus according to the present invention is shown in the form of flow chart. It is to be noted that the explanation is given collectively to the entire apparatus rather than separately to the measuring main unit 111 and the display case section 131. First of all, a person to be measured presses the power switch 135 disposed in the display case section 131 (Step 101). Thereby, the daily-life disability related physical information determining apparatus is activated into an operative mode, and a query screen appears on the display 142 requesting the person to be measured to determine whether or not a previously determined result should be indicated (Step 102).

Subsequently, the person to be measured, if he/she does not want the previously determined result to be indicated (NO in Step 103), presses the confirmation switch 139b representing "NO", thereby switching the screen (Step 104). Through this step, a currently determined result screen is made appear in the display 142 (Step 108).

Otherwise, the person to be measured, if he/she wants the previously determined result to appear on the screen (YES in Step 103), presses the confirmation switch 139a representing "YES", thereby switching the screen (Step 105). Through this step, a previously determined result screen is made appear on the display 142 (Step 106). Subsequently, to switch from this indication of the previously determined result to the indication of the currently determined result, the confirmation switch 139a representing "YES" is pressed (Step 107).

Subsequently, the currently determined result screen indicates thereon a set of information particular to an individual, consisting of a personal number, a sex, an age, a height and a body weight, and also a set of result information consisting of a lower limb muscle mass, an upper limb muscle mass, a left arm muscle mass, a right arm muscle mass, a left leg muscle mass, a right leg muscle mass, an entire body muscle mass, a leg muscle strength, an equilibration, a walking ability, a fall-down disabled level, a bone fracture disabled level, a osteoporosis disabled level, a hyperlipemia disabled level and an active motion disabled level, as shown in FIG. 15 (Step 108). In this regard, since the currently determined result screen in Step 108 is in a state as before the determination, these values are indicated as 0 "zero".

If the set of information particular to the individual consisting of consisting of the personal number, the sex, the age and the height has not yet set in the currently determined result screen in said Step 108 (NO in Step 109), then the person to be measured sets the information particular to the individual (Step 110). To set the information particular to the individual, the selection switch 140 shall be pressed to switch the cursor to the personal number field by the use of switching property in which each pressing operation of said selection switch 140 can switch the cursor to respective fields of personal number, sex, age and height, in sequence. Then, the ten key 136 is used to input an unregistered personal number, and the selected personal number is set by pressing the confirmation switch 139a representing "YES". In next operation, in which the cursor is switched to the field of sex, the ten key 136 is pressed to input the number corresponding to the appropriate sex and then the confirmation switch 139a representing "YES" is pressed to set the sex of the subject. In next operation, in which the cursor is switched to the field of age, the ten key 136 is pressed to input the age and then the confirmation switch 139a representing "YES" is pressed to set the age of the subject. In next operation, the ten key 136 is used to input the height and then the confirmation switch 139a representing "YES" is pressed to set the height of the subject. In case of wrong entry by the ten key 136, the clear key 138 should be pressed to reset the value in the current input field, and then the ten key 136 is pressed again to input a right value for setting.

Subsequently, if the set of information particular to the individual consisting of the personal number, the sex, the age and the height has been already set in the currently determined result screen in Step 108 (YES in Sep 109) or after Step 110, the person to be measured steps on the measuring platform 113 in the standing state such that the sole of each foot may be placed across the current-carrying electrode 115a and the measuring electrode 115b so as to come in contact with both electrodes. Then, the weight signal obtained during this measurement is transmitted from the weight sensor 119 via the weight measuring device 120 to the controller 123, which in turn determines the weight value, and the determined weight values is transmitted via the electric cord 143 and the input/output controller 134 to the display 142, which in turn indicates thereon the weight value as the information particular to the individual (Step 111).

In the following step, the person to be measured grips the measuring hand rail 114 such that the palm of each hand may be placed across the current-carrying electrode 115a and the measuring electrode 115b so as to come in contact with both electrodes, while remaining in said standing position. Subsequently, the bio-impedance at respective sites in the living body (body) is measured in a method as disclosed in U.S. Pat. No. 6,490,481, the entire disclosure of which is incorporated herein by reference (Step 112). Then, the measured bio-impedance at respective sites and the previously measured and entered secondary physical information (the weight, height, sex and age) are used to determine the values relating to the body constitution (the entire body muscle mass, the muscle mass in respective sites of the body) according to the arithmetic expressions in the controller 123, and the determined values relating to the body constitution are stored in the storage device 122 and at the same time transmitted via the electric cord 143 and the input/output controller 134 to the display 142, which in turn indicates the determined values on its screen (Step 113).

In the next step, the values relating to the body constitution stored in the storage device 122 and the previously measured and entered secondary physical information are used to determine the values relating to the basic physical strength (the leg muscle strength, the equilibration) and the values relating to the daily-life disability (the fall-down disabled level, the bone fracture disabled level, the osteoporosis disabled level and the hyperlipemia level) according to the equations (7) through (12) in the controller 123, and then the determined various results are stored in the storage device 122 and at the same time transmitted via the electric cord 143 and the input/output controller 134 to the display 142, which in turn indicates the determined results on its screen (Step 114).

Subsequently, the values relating to the basic physical strength stored in the storage device 122 and the previously measured and entered secondary physical information are used to determine the value relating to the motive ability (the waling ability) and the value relating to the daily-life disability (the active motion disabled level) according to the equations (13) and (14) in the controller 123, and the determined results are stored in the storage device 122 and at the same time transmitted via the electric cord 143 and the input/output controller 134 to the display 142, which in turn indicates the determined values on its screen (Step 115).

In the next step, if the indication of the display 142 is not switched to the graphical representation (NO in the step 116), the power switch 135 is pressed to end the series of procedures (Step 118). On the other hand, if the indication of the display 142 is switched (YES in Step 116), the selection switch 140 is pressed, thereby providing such a graphical representation as shown in FIGS. 16 through 18 on the screen (Step 117). Then, the power switch 135 is pressed to end the series of procedures (Step 118).

As described above, the daily-life disability related physical information determining apparatus according to the second embodiment of the present invention obtains the values relating to the physical condition consisting of the leg muscle mass and the entire body muscle mass as well as the secondary physical information consisting of the sex, the age, the height and the weight by the acquisition means 101. Then, based on those acquired values or information, the specification means 103 specifies the physical information on the physical strength related phase of the daily-life disability consisting of the leg muscle strength, the equilibration, the fall-down disabled level, the bone fracture disabled level, the osteoporosis disabled level and the hyperlipemia disabled level for the aged person placed as the subject, which is to be stored in the storage means 102. The specification means 103 further specifies the physical information on the physical strength related phase of the daily-life disability consisting of the walking ability and the active motion disabled level for the aged person placed as the subject, which is to be stored in the storage means 102. Then, the output means 104 outputs the specified results, so that the apparatus may provide automatically the highly accurate determination of the physical information on the physical strength related phase of the daily-life disability.

It is to be appreciated that although in the second embodiment of the present invention described above, the example in which the muscle mass (of the entire body as well as the respective sites of the body) is used as the value relating to the body constitution has been employed for the description, other parameter may be used so far as it may affect the physical strength involving in the daily-life disability, such as a lean body mass (of the entire body or the respective sites of the body) and/or a BCM ((Body Cell Mass: a total mass of cells conducting an oxidization to obtain energy) of the entire body or the respective sites of the body). Further, although the example in which the leg muscle strength and/or the equilibration are used as the value relating to the basic physical strength has been employed for the description, other parameter may be used so far as it may be considered as the physical strength factor which may cause the daily-life disability, such as the entire body muscle strength and/or the muscle strength of other respective sites of the body. Further, although the example in which the walking ability is used as the value relating to the motive ability, other parameter such as an ability for maneuvering may be used, so far as it may be considered to be a motive ability composed of a plurality of physical strength factors which may cause the daily-life disability by correlating to one another. Further, although the example in which the fall-down disabled level, the bone fracture disabled level, the osteoporosis disabled level and the hyperlipemia disabled level are used as the values relating to the daily-life disability has been employed for the description, other parameter may also be used, so far as it may indicative of the occurrence rate of the disability affective to the daily life in association with the physical strength. Still further, the example in which the body weight, the height, the age and the sex are used as the secondary physical information has been employed for the description, other information may be used, so far as it can be the information relating to the body, which may be an aid to the value relating to the physical condition.

Still further, although the example in which the value relating to the body constitution is used as the value relating to the physical condition has been employed for the description, the value relating to the basic physical strength and/or the value relating to the motive ability may be used as well.

Yet further, although the example in which the value relating to the basic physical strength, the value relating to the motive ability and the value relating to the daily-life disability are used as the physical information on the physical strength related phase of the daily-life disability has been employed for the description, other information may be used, so far as it can be the information relating to the daily-life disability resultant from the physical strength and/or the information on the body having a phase relating to the physical strength which may be a factor to cause the daily-life disability.

Further, a plurality of values relating to the physical conditions may be used in carrying out the invention. In one exemplary method, the acquisition means 101 may measure the leg muscle mass representing the value relating to the body constitution and also the body weight representing the secondary physical information, and may further acquire the leg muscle strength and the equilibration representing the values relating to the basic physical strength and also the height, the age and the sex as the secondary physical information through the input operation, and then the specification means 103 may use the following equation (15) stored in the storage means 102 to determine the walking ability representing the physical information on the physical strength related phase of the daily-life disability, thereby making the specification. As discussed above, upon determining the physical information on the physical strength related phase of the daily-life disability, the use of a plurality of parameters having principal relation, such as the values relating to the physical condition, may help provide a highly accurate estimation.

The equation (15) may be expressed as follows:

$$L_7=k_7 \times X_{11}+x_3 \times L_1+e_3 \times L_2+s_9 \times H+u_9 \times W+v_9 \times A+w_9 \times S+d_9 \quad (15)$$

where, respective symbols in the above equation are designated as follows:

$L_7$: walking ability,
$X_{11}$: leg muscle mass,
$L_1$: leg muscle strength,
$L_2$: equilibration,
H: height,
W: weight,
A: age,
S: sex, and
$k_7, x_3, e_3, s_9, u_9, v_9, w_9, d_9$: coefficient.

Although in the above embodiment, such an example has been employed for the description in which the specification means 103 specifies the physical information on the physical strength related phase of the daily-life disability associated with the value relating to the physical condition and the secondary physical information, and further specifies another physical information on the physical strength related phase of the daily-life disability associated with said specified physical information on the physical strength related phase of the daily-life disability and the secondary physical information, the specification means 103 may further specify yet another physical information on the physical strength related phase of the daily-life disability associated with said specified another physical information on the physical strength related phase of the daily-life disability. For example, the specification may be carried out in such a way that the walking ability determined from the equation (13) and the already obtained secondary information consisting of the age, the sex and the body weight are applied to the following equation (16) to determine the fall-down disabled level.

The equation (16) may be expressed as follows:

$$L_3=x_4 \times L_7+u_{10} \times W+v_{10} \times A+w_{10} \times S+d_{10} \quad (16)$$

where, respective symbols in the above equation are designated as follows:

$L_3$: fall-down disabled level,
$L_7$: walking ability,
W: weight,
A: age,
S: sex, and
$X_4, u_{10}, v_{10}, w_{10}, d_{10}$: coefficient.

Further, although in the above embodiment, such an example has been employed for the description in which upon determining the physical information on the physical strength related phase of the daily-life disability, the value relating to the physical condition that might be a primary factor and the secondary physical information that might be a secondary factor are used, the determination may be made based on exclusively the value relating to the physical condition that might be the primary factor of the daily-life disability. For example, the specification may be made in such a way that the acquisition means 101 obtains the leg muscle strength and the equilibration representing the values relating to the basic physical strength through the input operation, and then the specification means 103 uses the following equation (17) stored in the storage means 102 to determine the walking ability representing the physical information on the physical strength related phase of the daily-life disability.

$$L_7=x_5 \times L_1+e_4 \times L_2+d_{11} \quad (17)$$

where, respective symbols in the above equation are designated as follows:

$L_7$: walking ability,
$L_1$: leg muscle strength,
$L_2$: equilibration,
$x_5, e_4, d_{11}$: coefficient.

Further, although in the above embodiment, such an example has been employed for the description in which the display means 141 is used as the output means 104, the output means 104 may be implemented by a terminal for outputting the data to other device such as a personal computer.

Further, although in the above embodiment, such an example has been employed for the description in which the leg muscle strength is exclusively determined as the physical information on the physical strength related phase of the daily-life disability, an alternative method may be employed in which the controller 123 uses a similar arithmetic expression stored in the storage device 122 to determine the muscle strength in other respective sites of the body, and then the results on the muscle strength in respective sites of the body are indicated on the display means 142 similarly to FIG. 16.

Further, although in the above embodiment, such an example has been employed for the description in which upon determining the active motion disabled level, the expression of multi-regression, such as the equations (13) and (14) is used, the logistic regression model as expressed in the following equations (18) and (19) may be used.

The equations (18) and (19) are expressed as follows:

$$\log \{P_1/(1-P_1)\} = x_{12} \times L_1 + e_{12} \times L_2 + s_{12} \times H + u_{12} \times W + v_{12} \times A + w_{12} \times S + d_{12} \quad (18)$$

$$\log \{P_2/(1-P_2)\} = x_{13} \times L_1 + e_{13} \times L_2 + s_{13} \times H + u_{13} \times W + v_{13} \times A + w_{13} \times S + d_{13} \quad (19)$$

where, respective symbols in the above equations are designated as follows:

$P_1$: walking ability,
$P_2$: active motion disabled level,
$L_1$: leg muscle strength,
$L_2$: equilibration,
H: height,
W: weight,
A: age,
S: sex, and $x_{12}$, $x_{13}$, $e_{12}$, $e_{13}$, $s_{12}$, $s_{13}$, $u_{12}$, $u_{13}$, $v_{12}$, $v_{13}$, $w_{12}$, $w_{13}$, $d_{12}$, $d_{13}$: coefficient.

Further, although the specification means 103 has made a determination by carrying out the arithmetic operation for the physical information on the physical strength related phase of the daily-life disability based on the arithmetic expression for determining the physical information on the physical strength related phase of the daily-life disability stored in the storage means 102, an alternative method may be employed in which a corresponding relation table for determining the physical information on the physical strength related phase of the daily-life disability is stored in the storage means 102 and then the specification means 103 makes a specification by selecting specific physical information on the physical strength related phase of the daily-life disability.

EFFECT OF THE INVENTION

As described above, since the daily-life disability related physical information determining apparatus according to one aspect of the present invention specify in the specification means the active motion disabled level stored in the storage means based on the values relating to a plurality of different types of physical conditions acquired in the acquisition means, therefore the active motion disabled level can be determined automatically thereby making the using procedure of the apparatus simple and easy.

Further, since the present invention has employed input means and/or measuring means as the acquisition means, with which the value relating to the physical condition can be obtained easily, the apparatus can be used in a simple and easy manner.

Further, since the apparatus of the present invention specifies in the specification means the first advice information stored in the storage means based on the active motion disabled level acquired in the specification means, therefore the first advice information on the active motion disabled level can be received automatically.

Further, since the apparatus of the present invention specifies in the specification means the second advice information stored in the storage means based on the value relating to each individual physical condition among the plurality of different types of physical conditions acquired in the acquisition means, therefore the second advice information on the value relating to each individual physical condition can be received automatically.

Still further, since the present invention has employed the active motion disabled level associated with values relating to a plurality of different types of physical conditions with weighting factors applied thereto, therefore an highly accurate estimation can be provided.

Further, since the present invention has employed the active motion level for the aged person placed as the subject, therefore a higher utility value can be provided.

Further, since the present invention has employed display means as the output means, which may provide a graphical representation of the active motion disabled level associated with the axis of the graph representing the value relating to each individual physical condition among a plurality of different types of physical conditions, therefore the relationship between the value relating to each individual physical condition among the plurality of different types of physical conditions and the active motion disabled level can be grasped easily and visually.

Further, since the present invention has employed those values relating to a muscle, a body fat, a lean body, a leg lean body, a gravity center sway, an intracellular fluid, an extracellular fluid, and a pulse differential between sitting position and standing position, all of which have good relation with the active motion disabled level, as the values relating to a plurality of different types of physical conditions, therefore a highly accurate result can be obtained, and in addition, those value can be measured especially in a simple manner with only a small load applied to the body.

Since the daily-life disability related physical information determining apparatus according to another aspect of the present invention specifies in the specification means the physical information on the physical strength related phase of the daily-life disability stored in storage means based on the value relating to the physical condition acquired in the acquisition means, therefore the physical information on the physical strength related phase of the daily-life disability can be determined automatically thereby making the using procedure of the apparatus simple and easy.

Since said apparatus of the present invention further specifies in the specification means another physical information on the physical strength related phase of the daily-life disability stored in the storage means, based on the physical information on the physical strength related phase of the daily-life disability specified previously in the specification means, therefore the wide range of different physical information on the physical strength related phase of the daily-life disability can be determined automatically all at once thereby making the using procedure of the apparatus simple and easy.

Further, since said apparatus of the present invention has employed the input means and/or the measuring means as the acquisition means, with which the value relating to the physical condition can be obtained easily, the using procedure of the apparatus can be made simple and easy.

Further, since the result is indicated on the display means, the result can be visually perceived.

Further, since the physical information on the physical strength related phase of the daily-life disability is provided in a graphical representation, therefor the result can be easily turned into an image thus facilitating the perception thereof.

Further, since the present invention has employed the physical information on the physical strength related phase of the daily-life disability for the aged person placed as the subject, therefore a higher utility value can be obtained.

Further, since in the present invention, a value relating to the body constitution, a value relating to the basic physical strength, and a value relating to the motive ability have been employed as the values relating to the physical condition, and also a value relating to the basic physical strength, a value relating to the motive ability and a value relating to the daily-life disability have been employed as the physical information on the physical strength related phase of the daily-life disability, a highly accurate result can be obtained because of good relationship between corresponding items.

Further, since in the present invention, especially, a lean body mass, a muscle mass, a BCM, a muscle strength, an equilibration and a walking ability have been employed as the values relating to the physical condition, and also a muscle strength, an equilibration, a walking ability, a fall-down disabled level, a bone fracture disabled level, an osteoporosis disabled level, a hyperlipemia disabled level and an active motion disabled level have been employed as the physical information on the physical strength related phase of the daily-life disability, a highly accurate result can be obtained because of particularly good relationship between corresponding items.

Since the daily-life disability related physical information determining apparatus according to yet another aspect of the present invention specifies in the specification means the physical information on a physical strength related phase of a daily-life disability stored in the storage means, based on the value relating to the physical condition as well as the secondary physical information acquired in the acquisition means, therefore the physical information on the physical strength related phase of the daily-life disability can be determined automatically thus making the using procedure of the apparatus simple and easy. In addition, since the apparatus of the present invention has made a determination by taking not only the value relating to the physical condition but also the secondary information into account, therefore a highly accurate result can be obtained.

Further, since said apparatus of the present invention further specifies in the specification means another physical information on the physical strength related phase of the daily-life disability stored in the storage means, based on the physical information on the physical strength related phase of the daily-life disability specified previously in the specification means as well as the secondary physical information acquired in said acquisition means, therefore wide range of different physical information on the physical strength related phase of the daily-life disability can be determined automatically all at once with high accuracy thus making the using procedure of the apparatus simple and easy.

Further, since said apparatus of the present invention has employed the input means and/or the measuring means as the acquisition means, with which the value relating to the physical condition and the secondary physical information can be obtained easily, therefore the using procedure of the apparatus can be made simple and easy.

Further, since the result is indicated on the display means, the result can be visually perceived.

Further, since the physical information on the physical strength related phase of the daily-life disability is provided in a graphical representation, therefor the result can be easily turned into an image thus facilitating the perception thereof.

Further, since the present invention has employed the physical information on the physical strength related phase of the daily-life disability for the aged person placed as the subject, therefore a higher utility value can be obtained.

Further, since in the present invention, a value relating to the body constitution, a value relating to the basic physical strength, and a value relating to the motive ability have been employed as the values relating to the physical condition, and also a value relating to the basic physical strength, a value relating to the motive ability and a value relating to the daily-life disability have been employed as the physical information on the physical strength related phase of the daily-life disability, an extremely highly accurate result can be obtained because of good relationship between corresponding items.

Further, since in the present invention, especially, a lean body mass, a muscle mass, a BCM, a muscle strength, an equilibration and a walking ability have been employed as the values relating to the physical condition, and an age, a sex, a height and a body weight have been employed as the secondary information, and also a muscle strength, an equilibration, a walking ability, a fall-down disabled level, a bone fracture disabled level, an osteoporosis disabled level, a hyperlipemia disabled level and an active motion disabled level have been employed as the physical information on the physical strength related phase of the daily-life disability, therefore an extremely highly accurate result can be obtained because of particularly good relationship between corresponding items.

What is claimed is:

1. A daily-life disability related physical information determining apparatus, comprising acquisition means, storage means, specification means and output means, wherein said acquisition means acquires at least two physical condition values selected from a group consisting of an entire body muscle mass, a percent entire body muscle, a leg muscle mass, a percent leg muscle, an arm muscle mass, a percent body fat, a body fat mass, a lean body mass, a percent lean body, a leg lean body mass, a percent leg lean body, an arm lean body mass, a gravity center sway distance, a gravity center sweep area, an extracellular fluid volume, an intracellular fluid volume, and a pulse differential count between sitting position and standing position;

said storage means stores an active motion disabled level, which have been associated with the at least two values acquired by said acquisition means;

said specification means specifies the active motion disabled level stored in said storage means based on the at least two values acquired by said acquisition means; and said output means outputs the active motion disabled level specified by said specification means.

2. The apparatus according to claim 1, wherein said storage means further stores a first advice information and a second advice information, the first advice information being designated as text information presented as an advice to a person to be measured, including a warning, an evocation, a reminder and a caution with respect to a result of the active motion disabled level specified by said specification means, and the second advice information being designated as text information presented as an advice to the person to be measured, including a warning, an evocation, a reminder and a caution with respect to a result for each of the at least two physical condition values acquired by said acquisition means, said specification means further specifies the first advice information stored in said storage means based on the previously specified active motion disabled level and the second advice information stored in said storage means based on each of the at least two values acquired by said acquisition means, and said output means further output, at the same time, the first information and the second information specified by said specification means.

3. The apparatus according to claim 1, wherein said output means is display means for indicating a result of the active motion disabled level specified by said specification means, the display means indicating the result in a color associated with the active motion disabled level to provide a graphical representation of the active motion disabled level, by associating the result with a graph having a graph axis which is associated with each of the at least two physical condition values acquired by said acquisition means.

4. The apparatus according to anyone of claim 1 or 3, wherein said acquisition means acquires anyone at least two physical condition values selected from a group consisting of the percent body fat, the body fat mass, the lean body mass, the percent lean body, the leg lean body mass, the percent leg lean body, the arm lean body mass, the gravity center sway distance, the gravity center sweep area, the extracellular fluid volume, the intracellular fluid volume and the pulse differential count between sitting position and standing position;

said storage means stores the following equations $U_1$, $U_2$ and Y where:

$U_1 = \{(X_5/X_4) - 1.35\}/1.35$ $X_4$ indicates the extracellular fluid volume, $X_5$ indicates the intracellular fluid volume, and $U_1$ indicates a weighting coefficient;

if $X_6 \leq 10$ or $100 < X_6$, then $U_2 = 2$ and if $10 < X_6 < 100$, then $U_2 = 1$ $X_6$ indicates the pulse differential count between sitting position and standing position and $U_2$ indicates a weighting coefficient; and $Y = (a \times X_1 + b \times X_2 \times U_1 + c \times X_3 + z) \times U_2$ $X_1$ indicates anyone of the percent body fat and the body fat mass; $X_2$ indicates anyone of the lean body mass, the percent lean body, the leg lean body mass, the percent leg lean body and the arm lean body mass; $X_3$ indicates any one of the gravity center sway distance and the gravity center sweep area; a, b, c, z respectively indicates a coefficient; and Y indicates the active motion disabled level; and said specification means specifies the active motion disabled level by substituting the extracellular fluid volume, the intracellular fluid volume, and the pulse differential count between sitting position and standing position, each acquired by said acquisition means, into the equations $U_1$ and $U_2$ stored in said storage means, so as to determine the weighting coefficients, and further substituting the determined weighting coefficients with anyone of the percent body fat, the body fat mass, the lean body mass, the percent lean body, the leg lean body mass, the percent leg lean body, the arm lean body mass, the gravity center sway distance and the gravity center sweep area, each acquired by said acquisition means, into the equation Y stored in said storage means.

5. A daily-life disability related physical information determining apparatus, comprising acquisition means, storage means, specification means and output means, wherein said acquisition means acquires at least one physical condition value selected from a lean body mass, a body muscle mass, and a body cell mass (BCM);

said storage means stores at least one value selected from a muscle strength, an equilibration, a walking ability, a fall-down disabled level, a bone fracture disabled level, an osteoporosis disabled level, a hyperlipemia disabled level and an active motion disabled level, which have been associated with the at least one physical condition value acquired by said acquisition means;

said specification means specifies the at least one value stored in said storage means based on the at least one physical condition value acquired by said acquisition means; and said output means outputs the at least one value specified by said specification means.

6. The apparatus according to claim 5, wherein said storage means further stores another at least one of the muscle strength, the equilibration, the walking ability, the fall-down disabled level, the bone fracture disabled level, the osteoporosis disabled level, the hyperlipemia disabled level and the active motion disabled level, which have been associated with the at least one specified by said specification means, said specification means further specifies another at least one stored in said storage means based on the previously specified at least one, and said output means further output another at least one specified by said specification means.

7. A daily-life disability related physical information determining apparatus, comprising acquisition means, storage means, specification means and output means, wherein said acquisition means acquires at least one physical condition value selected from a lean body mass, a body muscle mass, and a BCM; and one or more of the following factors: an age, a sex, a height and a weight;

said storage means stores at least one value selected from a muscle strength, an equilibration, a walking ability, a fall-down disabled level, a bone fracture disabled level, an osteoporosis disabled level, a hyperlipemia disabled level and an active motion disabled level, which have been associated with the at least one physical condition value and the at least one parameter, each acquired by said acquisition means;

said specification means specifies the at least one value stored in said storage means based on the at least one physical condition value and the at least one parameter acquired by said acquisition means; and said output means outputs the at least one value specified by said specification means.

8. The apparatus according to claim 7, wherein said storage means further stores another at least one of the muscle strength, the equilibration, the walking ability, the fall-down disabled level, the bone fracture disabled level, the osteoporosis disabled level, the hyperlipemia disabled level and the active motion disabled level, which have been associated with the at least one specified by said specification means, said specification means further specifies another at least one stored in said storage means based on the previously specified at least one and the at least one of the age, the sex, the height and the weight, each acquired by said acquisition means, and said output means further output another at least one specified by said specification means.

9. The apparatus according to claim 7, wherein said acquisition means acquires a leg muscle mass, the height, the weight, the age and the sex;

said storage means stores at least one of the following equations:

$L_1 = k_1 \times X_{11} + s_1 \times H + u_1 \times W + v_1 \times A + w_1 \times S + d_1$ $L_2 = k_2 \times X_{11} + s_2 \times H + u_2 \times W + v_2 \times A + w_2 \times S + d_2$ $L_3 = k_3 \times X_{11} + s_4 \times H + u_3 \times W + v_3 \times A + w_3 \times S + d_3$ where $X_{11}$ indicates the leg muscle mass; H indicates the height; W indicates the weight; A indicates the age; S indicates the sex; $k_1$–$k_3$, $s_1$–$s_3$, $u_1$–$u_3$, $V_1$–$V_3$, $w_1$–$w_3$ and $d_1$–$d_3$ each indicate a coefficient; $L_1$ indicates a leg muscle strength; $L_2$ indicates the equilibration and $L_3$ indicates the fall-down disabled level; and said specification means determines at least one of the leg muscle strength, the equilibration and the fall-down disabled level by substituting the leg muscle mass, the height, the weight, the age, and the sex, each acquired by said acquisition means, into the at least one of the equations $L_1$, $L_2$ and $L_3$ stored in said storage means.

10. The apparatus according to claim 7, wherein said acquisition means acquires an entire body muscle mass, the height, the weight, the age and the sex;

said storage means stores at least one of the following equations:

$$L_4 = k_4 \times X_{12} + s_4 \times H + u_4 \times W + v_4 \times A + w_4 \times S + d_4$$

$$L_5 = k_5 \times X_{12} + s_5 \times H + u_5 \times W + v_5 \times A + w_5 \times S + d_5$$

$$L_6 = k_6 \times X_{12} + s_6 \times H + u_6 \times W + v_6 \times A + w_6 \times S + d_6$$

where $X_{12}$ indicates the entire body muscle mass, H indicates the height, W indicates the weight, A indicates the age, S indicates the sex, $k_4$–$k_6$, $s_4$–$s_6$, $u_4$–$u_6$, $v_4$–$v_6$, $w_4$–$w_6$ and $d_4$–$d_6$ each indicate a coefficient, $L_4$ indicates the bone fracture disabled level, $L_5$ indicates the osteoporosis disabled level and the $L_6$ indicates the hyperlipemia disabled level; and said specification means determines at least one of the bone fracture disabled level, the osteoporosis disabled level and the hyperlipemia disabled level by substituting the entire body muscle mass, the height, the weight, the age, and the sex, each acquired by said acquisition means, into the at least one of the equations $L_4$, $L_5$ and $L_6$ stored in said storage means.

11. The apparatus according to claim 9, wherein said storage means further stores at least one of the following equations:

$$L_7 = x_1 \times L_1 + e_1 \times L_2 + s_7 \times H + u_7 \times W + v_7 \times A + w_7 \times S + d_7$$

$$L_8 = x_2 \times L_1 + e_2 \times L_2 + s_8 \times H + u_8 \times W + v_8 \times A + w_8 \times S + d_8$$

where $L_1$ indicates the leg muscle strength, $L_2$ indicates the equilibration, H indicates the height, W indicates the body weight, A indicates the age, S indicates the sex, $x_1$, $x_2$, $e_1$, $e_2$, $s_7$, $s_8$, $u_7$, $u_8$, $v_7$, $v_8$, $w_7$, $w_8$, $d_7$ and $d_8$, each indicate a coefficient, $L_7$ indicates the walking ability and $L_8$ indicates the active motion disabled level; and said specification means further determines at least one of the walking ability and the active motion disabled level by substituting the leg muscle strength and the equilibration, each determined previously, and the height, the weight, the age, and the sex, each acquired by said acquisition means, into the at least one of the equations $L_7$ and $L_8$ stored in said storage means.

12. The apparatus according to claim 11, wherein said storage means further stores the following equations:

$$L_3 = x_4 \times L_7 + u_{10} \times W + v_{10} \times A + w_{10} \times S + d_{10},$$

where $L_7$ indicates the walking ability; W indicates the body weight; A indicates the age; S indicates the sex; $x_4$, $u_{10}$, $v_{10}$, $w_{10}$ and $d_{10}$ each indicate a coefficient; $L_3$ indicates the fall-down disabled level; and said specification means further determines the fall-down disabled level by substituting the previously determined walking ability and the weight and the age, each acquired by said acquisition means, into the equation $L_3$ stored in said storage means.

13. The apparatus according to claim 9, wherein said storage means further stores the following equation:

$$L_7 = k_7 \times X_{11} + x_3 \times L_1 + e_3 \times L_2 + s_9 \times H + u_9 \times W + v_9 \times A + w_9 \times S + d_9,$$

where $X_{11}$ indicates the leg muscle mass; $L_1$ indicates the leg muscle strength; $L_2$ indicates the equilibration; H indicates the height; W indicates the weight; A indicates the age; S indicates the sex; $k_7$, $x_3$, $e_3$, $s_9$; $u_9$, $v_9$, $w_9$ and $d_9$ each indicate a coefficient; and $L_7$ indicates the walking ability; and said specification means further determines at least one of the walking ability and the active motion disabled level by substituting the leg muscle strength and the equilibration, each determined previously, and the height, the weight, the age, and the sex, each acquired by said acquisition means, into the at least one of the equations $L_7$ and $L_8$ stored in said storage means.

14. The apparatus according to claim 9, wherein said storage means further stores at least one of the following equations:

$$\log\{P_1/(1-P_1)\} = x_{12} \times L_1 + e_{12} \times L_2 + s_{12} \times H + u_{12} \times W + v_{12} \times A + w_{12} \times S + d_{12},$$

$$\log\{P_2/(1-P_2)\} = x_{13} \times L_1 + e_{13} \times L_2 + s_{13} \times H + u_{13} \times W + v_{13} \times A + w_{13} \times S + d_{13},$$

where $L_1$ indicates the leg muscle strength; $L_2$ indicates the equilibration; H indicates the height; W indicates the weight; A indicates the age; S indicates the sex; $x_{12}$, $x_{13}$, $e_{12}$, $e_{13}$, $s_{12}$, $s_{13}$, $u_{12}$, $u_{13}$, $v_{12}$, $v_{13}$, $v_{12}$, $v_{13}$, $w_{12}$, $w_{13}$, $d_{12}$, and $d_{13}$ each indicate a coefficient; $P_1$ indicates the walking ability; and $P_2$ indicates the active motion disabled level; and said specification means further determines at least one of the walking ability and the active motion disabled level by substituting the leg muscle strength and the equilibration, each determined previously, and the height, the weight, the age, and the sex, each acquired by said acquisition means, into the at least one of the $\log\{P_1/(1-P_1)\}$ and $\log\{P_2/(1-P_2)\}$ equations stored in said storage means.

* * * * *